(12) United States Patent
Minor

(10) Patent No.: US 11,798,685 B2
(45) Date of Patent: Oct. 24, 2023

(54) DIAGNOSTIC METHODS AND DEVICES FOR CONTROLLING ACUTE GLYCEMIA

(71) Applicant: James M. Minor, Newark, DE (US)

(72) Inventor: James M. Minor, Newark, DE (US)

( * ) Notice: Subject to any disclaimer, the term of this patent is extended or adjusted under 35 U.S.C. 154(b) by 326 days.

(21) Appl. No.: 14/665,658

(22) Filed: Mar. 23, 2015

(65) Prior Publication Data

US 2015/0310178 A1 Oct. 29, 2015

Related U.S. Application Data

(63) Continuation-in-part of application No. 13/895,054, filed on May 15, 2013, now Pat. No. 9,465,910.

(60) Provisional application No. 62/051,943, filed on Sep. 17, 2014, provisional application No. 61/969,150, filed on Mar. 22, 2014, provisional application No. 61/647,165, filed on May 15, 2012.

(51) Int. Cl.
| | | |
|---|---|---|
| G16H 50/20 | (2018.01) | |
| G01N 33/66 | (2006.01) | |
| G16H 50/30 | (2018.01) | |
| G16H 50/50 | (2018.01) | |
| G16Z 99/00 | (2019.01) | |

(52) U.S. Cl.
CPC ............ *G16H 50/20* (2018.01); *G01N 33/66* (2013.01); *G16H 50/30* (2018.01); *G16H 50/50* (2018.01); *G16Z 99/00* (2019.02)

(58) Field of Classification Search
CPC ........ G16H 50/20; G16H 50/50; G16H 50/30; G16Z 99/00; G01N 33/66
See application file for complete search history.

(56) References Cited

U.S. PATENT DOCUMENTS

| | | | |
|---|---|---|---|
| 5,009,230 A | | 4/1991 | Hutchinson |
| 5,141,868 A | | 8/1992 | Shanks et al. |
| 5,286,362 A | | 2/1994 | Hoenes et al. |
| 5,437,999 A | | 8/1995 | Diebold et al. |
| 5,507,288 A | * | 4/1996 | Bocker ................ A61B 5/0002 128/903 |
| 5,708,247 A | | 1/1998 | McAleer et al. |
| 5,951,836 A | | 9/1999 | McAleer et al. |
| D428,150 S | | 7/2000 | Ruf et al. |
| 6,241,862 B1 | | 6/2001 | McAleer et al. |
| 6,285,125 B1 | | 9/2001 | Mizuno |
| 6,413,410 B1 | | 7/2002 | Hodges et al. |
| 6,733,655 B1 | | 5/2004 | Davies et al. |
| 7,695,434 B2 | * | 4/2010 | Malecha ................ G16H 50/50 600/365 |
| 8,257,258 B2 | * | 9/2012 | Zocchi ................ A61B 5/1486 600/345 |
| 8,372,261 B2 | | 2/2013 | Feldman et al. |
| 8,409,093 B2 | | 4/2013 | Bugler |
| 8,425,416 B2 | | 4/2013 | Brister et al. |
| 2005/0159656 A1 | | 7/2005 | Hockersmith et al. |
| 2006/0253067 A1 | | 11/2006 | Staib et al. |
| 2007/0232872 A1 | | 10/2007 | Prough et al. |
| 2009/0018406 A1 | | 1/2009 | Yodfat et al. |
| 2009/0030398 A1 | | 1/2009 | Yodfat et al. |
| 2009/0048152 A1 | | 2/2009 | Yodfat et al. |
| 2009/0292180 A1 | | 11/2009 | Mirow |
| 2010/0330594 A1 | | 12/2010 | Hart et al. |
| 2010/0331651 A1 | | 12/2010 | Groll |
| 2011/0264378 A1 | * | 10/2011 | Breton ................ A61B 5/0002 702/19 |
| 2011/0319322 A1 | | 12/2011 | Bashan et al. |
| 2012/0191361 A1 | * | 7/2012 | Kovatchev ............. G06F 19/00 702/19 |
| 2012/0245556 A1 | | 9/2012 | Kovatchev et al. |
| 2012/0330119 A1 | | 12/2012 | Shaanan et al. |
| 2013/0030358 A1 | | 1/2013 | Yodfat et al. |
| 2013/0035865 A1 | | 2/2013 | Mayou et al. |
| 2013/0035871 A1 | | 2/2013 | Mayou et al. |
| 2013/0041343 A1 | | 2/2013 | Toumazou et al. |
| 2013/0085349 A1 | | 4/2013 | Shaanan et al. |
| 2013/0085358 A1 | | 4/2013 | Crouther et al. |
| 2013/0098775 A1 | | 4/2013 | Pei et al. |
| 2013/0102018 A1 | | 4/2013 | Schentag et al. |
| 2013/0102867 A1 | | 4/2013 | Desborough et al. |
| 2013/0103424 A1 | | 4/2013 | Brown |
| 2013/0108598 A1 | | 5/2013 | Oresic et al. |
| 2013/0112557 A1 | | 5/2013 | Javitt et al. |
| 2013/0311102 A1 | | 11/2013 | Minor |

OTHER PUBLICATIONS

Crenier, L .; "Poincaré Plot Quantification for Assessing Glucose Variability from Continuous Glucose Monitoring Systems and a New Risk Marker for Hypoglycemia: application to Type 1 Diabetes Patients Switching to Continuous Subcutaneous Insulin Infusion"; Mar. 13, 2014; 16(4): 247-254.*

Fishman, N. et al; "A method for analyzing temporal patterns of variability of a time series from Poincaré plots"; J Appl Physiol 113: 297-306, 2012.*

McCall, A. Al. et al; "A Novel Analytical Method for Assessing Glucose Variability: Using CGMS in Type 1 Diabetes Mellitus"; Diabetes Technology & Therapeutics; vol. 8, No. 6, 2006; p. 664-653.*

Kovachtev, B. P. et al; "Graphical and Numerical Evaluation of Continuous Glucose Sensing Time Lag"; Diabetes Technology & Therapeutics; vol. 11, No. 3, 2009; p. 139-143.*

Kovachtev, B. P. et al; "Quantifying Temporal Glucose Variability in Diabetes via Continuous Glucose Monitoring: Mathematical Methods and Clinical Application"; Diabetes Technology & Therapeutics; vol. 7, No. 6, 2005; p. 849-862.*

(Continued)

*Primary Examiner* — Jerry Lin

(57) ABSTRACT

Devices, systems and methods for monitoring glycemic levels in a patient, by calculate a plurality of blood glucose values from a plurality of blood samples taken, calculating a quantile of the blood glucose values taken over a period of days; and creating a Lorenz plot for the blood glucose values in the quantile.

5 Claims, 28 Drawing Sheets

(56) References Cited

OTHER PUBLICATIONS

Clarke, W. et al; "Statistical Tools to Analyze Continuous Glucose Monitor Data"; Diabetes Technology & Therapeutics; vol. 11, Supplement 1, 2009; p. S45-S54.*

Toichi, M. et al; "A new method of assessing cardiac autonomic function and its comparison with spectral analysis and coefficient of variation of R-R interval"; Journal of the Autonomic Nervous System 62 (1997) 79-84.*

Hnatkova K., et al; "Numeric processing of Lorenz plots of R-R intervals from long-term ECGs. Comparison with time-domain measures of heart rate variability for risk stratification after myocardial infarction", J Electrocardiol. 1995; 28 Suppl:74-80 (Year: 1995).*

View Kroll, M. H."Biological variation of glucose and insulin includes a deterministic chaotic component". Biosystems. 1999; 50:189-201. (Year: 1999).*

Holt, T. A.; "A chaotic model for tight diabetes control"; Diabetic Medicine (2002), 19, p. 274-278. (Year: 2002).*

Holt, T. A.; "Nonlinear Dynamics and Diabetes Control"; The Endocrinologist (2003); vol. 13, No. 6; p. 452-456. (Year: 2003).*

Molnár, G. A. et al; "The Poincaré Plot, but Not the Correlation R Value, Is a Good Marker of Temporal Variability of CGMS Data"; Diabetes Technology & Therapeutics. Dec. 2008. p. 506-507. (Year: 2008).*

Rigla, M. et al; "Real-Time Continuous Glucose Monitoring Together with Telemedical Assistance Improves Glycemic Control and Glucose Stability in Pump-Treated Patients". Diabetes Technology & Therapeutics. Jun. 2008. p. 194-199. (Year: 2008).*

Kovatchev BP, Shields D, Breton M. "Graphical and numerical evaluation of continuous glucose sensing time lag", Diabetes Technol Ther. Mar. 2009;11(3):139-43 (Year: 2009).*

Clarke W, Kovatchev B. "Statistical tools to analyze continuous glucose monitor data", Diabetes Technol Ther. Jun. 2009;11 Suppl 1 (Suppl 1):S45-54 (Year: 2009).*

Cohen et al., "Red cell life span heterogenicity in hematologically normal people is sufficient to alter HbA1c", Blood, Nov. 15, 2008, Abstract.

Kahn et al., "Translating the A1C Assay", Diabetes Care, vol. 31, No. 8, Aug. 2008, pp. 1704-1707.

Kroll, "Biological variation of glucose and insulin includes a deterministic chaotic component", Biosystems 50 91999) pp. 189-201.

Nathan et al., "Translating the A1c Assay into Estimated Average Glucose Values", Diabetes Care, 31:1473-1478, 2008.

The Art and Science of Diabetes Self-Management Education, American Association of Diabetes Educators, 2006, pp. 145, 218.

Wilson et al., "Persistence of Individual Variations in Glycated Hemoglobin", Diabetes Care, vol. 34, Jun. 2011, pp. 1315-1317.

PCT/US2015/022031 International Search Report, dated Jun. 18, 2015.

* cited by examiner

Typical DOX (DOE) for LRS

Design

| Run | angle | LnC | Lnr cycle | Y |
|-----|-------|-----|-----------|---|
| 1   | 150   | 3   | 3.69      |   |
| 2   | 300   | 6   | 2.995     |   |
| 3   | 0     | 4.5 | 3.69      |   |
| 4   | 150   | 4.5 | 2.995     |   |
| 5   | 150   | 6   | 2.3       |   |
| 6   | 0     | 4.5 | 2.3       |   |
| 7   | 300   | 3   | 2.995     |   |
| 8   | 300   | 4.5 | 3.69      |   |
| 9   | 150   | 6   | 3.69      |   |
| 10  | 0     | 6   | 2.995     |   |
| 11  | 150   | 3   | 2.3       |   |
| 12  | 300   | 4.5 | 2.3       |   |
| 13  | 150   | 4.5 | 2.995     |   |
| 14  | 0     | 3   | 2.995     |   |

Design Evaluation

Design Diagnostics

I Optimal Design
D Efficiency                       35.5994
G Efficiency                       79.90542
A Efficiency                       23.58722
Average Variance of Prediction     0.52004
Design Creation Time (seconds)     8.5

Two Lorenz cycles of data within one month provide an optimal design for the Lorenz Response Surface© (LRS)

FIG. 8

HiCGM98C11 indicates next-day acute glycemia.

HiCGM98C11 = 1 if Prob(next-day hyperglycemia)>0.50, where next-day hyperglycemia occurs if Q98 > 250 mg/dL 1. Truth table of predictions >>>>>>>>>>>>>>>>>>>>>>>>>>>>>>
Off-diagonals report error stat's.
Here 10 acute Q98 days were not recognized and 11 days were incorrectly called glycemic of 760 days. %-stats are also shown.

| | | Most Likely HiCGM98C11 | |
|---|---|---|---|
| Count | 0 | 1 | |
| Col % | | | |
| Row % | | | |
| HiCGM98C11 0 | 621 | 11 | 632 |
| | 98.42 | 8.53 | |
| | 98.26 | 1.74 | |
| 1 | 10 | 118 | 128 |
| | 1.58 | 91.47 | |
| | 7.81 | 92.19 | |
| | 631 | 129 | 760 |

2. Impact of Lorenz factors
*'s are significant <<<<<<<<<<<<<<<

| Source | Prob>ChiSq |
|---|---|
| Subject | <.0001* |
| Q98SyncAngle7[Subject] | 0.0975 |
| Q98SyncAngle7*Q98SyncAngle7[Subject] | 0.1379 |
| Q98SyncAngle7*Q98Lmn7[Subject] | 0.1129 |
| Q98SyncAngle7*Q98r7[Subject] | 0.0028* |
| Q98SyncAngle7*Q98SyncAngle7*Q98r7[Subject] | 0.0017* |
| Q98Lmn7[Subject] | <.0001* |
| Q98Lmn7*Q98Lmn7[Subject] | <.0001* |

3. Profiler relates Q98 Prob to Lorenz factors >>>>>>>>>>>
Near left axis (-3.3), the model starts predicting next-day glycemia.
Note for Q98
0 to -pi is lower half of Lorenz plot while -pi to -2pi is the upper half.

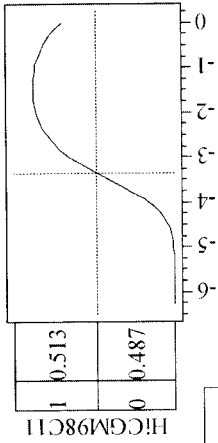

^^^^^^^^^^^^^^^^^^^^^^^^^^^^^^^^^^^^^^^^^^
The same format applies to LowCGM02C11 indicating next-day hypoglycemia.

DIAGNOSTIC METHODS AND DEVICES FOR CONTROLLING ACUTE GLYCEMIA

CROSS-REFERENCE

This application is a continuation-in-part application of Application Ser. No. 13/895,054, filed May 15, 2013, which is hereby incorporated herein, in its entirety, by reference thereto, and to which application we claim priority under 35 USC § 120.

Application Ser. No. 13/895,054 claims the benefit of U.S. Provisional Application No. 61/647,165, filed May 15, 2012, which application is hereby incorporated herein, in its entirety, by reference thereto.

This application claims the benefit of U.S. Provisional Application Nos. 61/969,150, filed Mar. 22, 2014 and 62/051,943, filed Sep. 17, 2014, both of which applications are hereby incorporated herein, in their entireties, by reference thereto.

FIELD OF THE INVENTION

This invention relates generally to the field of diagnostic processes, devices, and chaos physics for identifying, monitoring, and controlling acute glycemia.

BACKGROUND OF THE INVENTION

Chronic glycemia, commonly denoted AG, is the extreme persistent level of blood glucose (chronic BG) as measured by the A1C-assay and is related to diabetes progression and complications.

Acute glycemia is likely when chronic BG plus its acute volatility creates a significant presence at extreme critical levels clinically defined as hypo/hyper-glycemia. Anticipating such acute glycemia is a key factor in both the prevention of sudden serious/dangerous conditions as well as the clinical management of diabetes healthcare as described in established medical reference books (1,2).

Acute glycemia (hypo/hyper-BG levels) causes serious consequences to both patient and society in terms of serious injury and healthcare complications due to disease progression and disasters such as transportation/home accidents. However, as described in recent publications, attacks of acute glycemia cannot be usefully predicted due to the chaotic nature of BG.

There is a current need to diagnostic methods and devices that can usefully predict acute hypoglycemia.

SUMMARY OF THE INVENTION

According to one aspect of the present invention, a device for monitoring glycemic levels in a patient is provided, including: a housing; a processor coupled to memory; an interface for inputting to the processor; a display for displaying results of processing by said processor; and a port configured to receive a blood glucose monitoring strip that is used to take a blood sample from the patient, and from which the processor calculates a blood glucose value; wherein the processor, interface and port are contained in the housing, and wherein the interface is mounted in the housing; and wherein the processor is configured to: calculate a plurality of the blood glucose values from a plurality of blood samples taken from a plurality of the blood glucose monitoring strips; calculate a quantile of the blood glucose values taken over a period of days; create a Lorenz plot for the blood glucose values in the quantile; and display the Lorenz plot.

In at least one embodiment, the monitoring is real-time monitoring.

In at least one embodiment, the displayed Lorenz plot can be viewed by a user to identify days in which acute glycemia was experienced by the patient.

In at least one embodiment, the processor identifies days in which acute glycemia was experienced by the patient, based on values in the Lorenz plot, and displays days in which the acute glycemia was experienced.

In at least one embodiment, the processor calculates orbits for the quantile, and applies a quantitative model to the orbits to identify probability trends for acute glycemia, In at least one embodiment, the quantitative model comprises a single metric model.

In at least one embodiment, the quantitative model comprises a combined metrics model.

In at least one embodiment, the quantitative model comprises logistic regression based on functions of Lorenz factors from the Lorenz plot.

In at least one embodiment, the quantitative model comprises calculation of a Lorenz Response Surface (LRS).

According to another aspect of the present invention, a system for monitoring glycemic levels in a patient is provided that includes: a processor coupled to memory; and an interface for receiving input to and outputting from the processor; wherein the processor is configured to: receive or calculate a plurality of the blood glucose values from a plurality of blood samples taken from a plurality of the blood glucose monitoring strips; calculate a quantile of the blood glucose values taken over a period of days; create a Lorenz plot for the blood glucose values in the quantile; and output the Lorenz plot.

In at least one embodiment, the processor receives the blood glucose values from a blood glucose monitoring device.

In at least one embodiment, the processor identifies days in which acute glycemia was experienced by the patient, based on values in the Lorenz plot, and outputs days in which the acute glycemia was experienced.

In at least one embodiment, the processor calculates orbits for the quantile, and applies a quantitative model to the orbits to identify probability trends for acute glycemia, In at least one embodiment, the quantitative model comprises logistic regression based on functions of Lorenz factors from the Lorenz plot.

In at least one embodiment, the quantitative model comprises calculation of a Lorenz Response Surface (LRS).

According to another aspect of the present invention, a method of monitoring glycemia includes: receiving or calculating inter-day blood glucose values from blood samples taken from a patient on specified days; calculating a quantile from the inter-day blood glucose values; calculating orbits for the quantile; creating a Lorenz plot for the quantile; and identifying at least one of: one or more days during which extreme glycemia was experienced for the quantile, and prediction of when extreme glycemia is expected to be experienced for the quantile.

In at least one embodiment, the extreme glycemia is acute hypoglycemia or acute hyperglycemia.

In at least one embodiment, the method further includes applying quantitative model to the orbits to identify probability trends for extreme glycemia.

In at least one embodiment, the quantitative model comprises logistic regression based on functions of Lorenz factors from the Lorenz plot.

In at least one embodiment, the quantitative model comprises calculation of a Lorenz Response Surface (LRS).

These and other features of the invention will become apparent to those persons skilled in the art upon reading the details of the devices, systems and methods as more fully described below.

BRIEF DESCRIPTION OF THE DRAWINGS

The drawings further describe the present invention by illustration. Each drawing is referenced by corresponding figure reference characters within the "DETAILED DESCRIPTION OF THE INVENTION" section to follow.

FIG. 8 shows exemplary design of experiment values used for calculating Lorenz response surfaces, according to embodiments of the present invention.

FIG. 9 shows a diagram of tri-section evaluation for acute risk models, according to an embodiment of the present invention.

FIG. 19 illustrates a low risk Q02 single metric model, according to an embodiment of the present invention.

DETAILED DESCRIPTION OF THE INVENTION

Figures 1A, 1B:
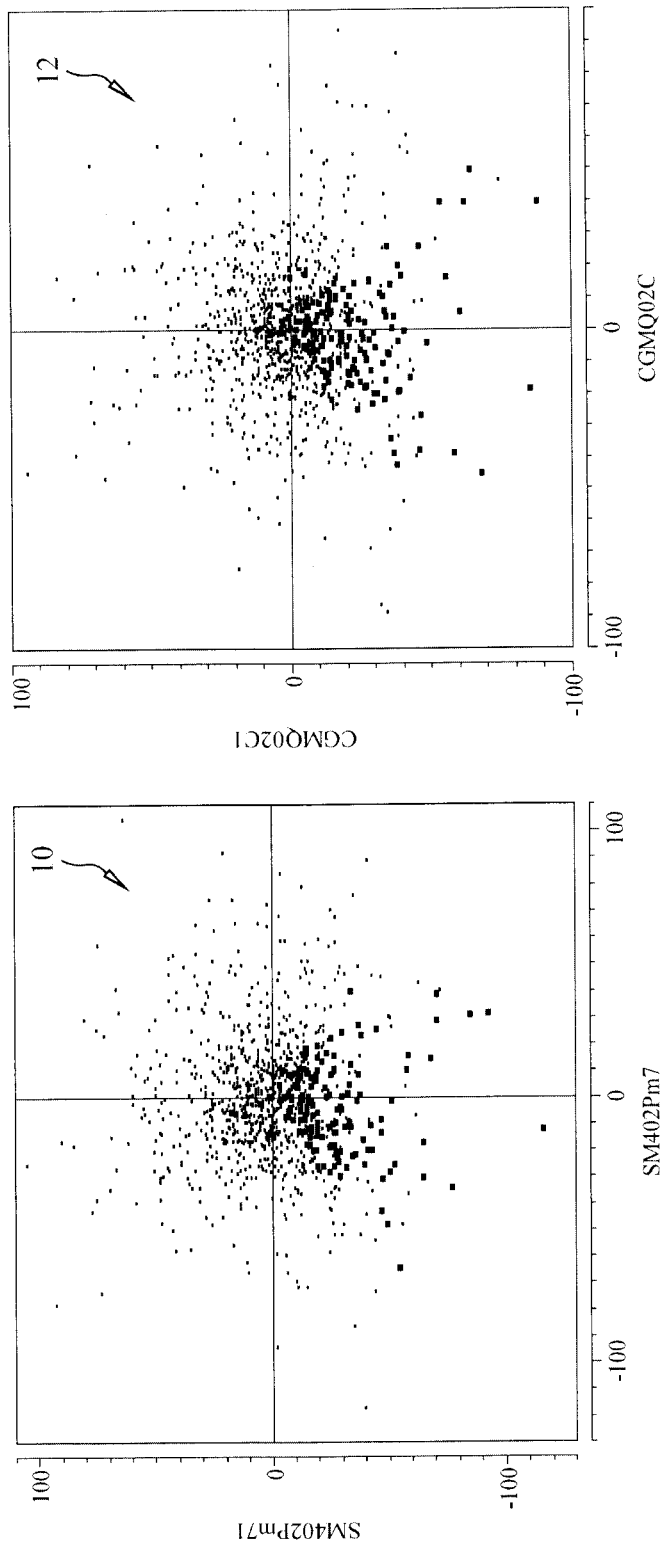
FIGS. 1A-1B show synchronized similarity of CGM and SMBG Quantiles using different Lorenz variables from CGM and SMBG profiles, according to an embodiment of the present invention.

Before the present devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a value" includes a plurality of such values and reference to "the cycle" includes reference to one or more cycles and equivalents thereof known to those skilled in the art, and so forth.

The publications discussed herein are provided solely for their disclosure prior to the filing date of the present application. The dates of publication provided may be different from the actual publication dates which may need to be independently confirmed.

Definitions

The acronym "BG" is used herein to refer to blood glucose. All blood glucose (BG) units described herein are blood-fluid concentration units, typically mg/dL (milligram/deciliter), unless noted otherwise.

The "daily BG mean" refers to a full-day average of BG levels provided by a high rate blood sampling device (continuous glucose monitoring (CGM) device) attached to a patient, typically sampling every 5 to 10 minutes. The daily mean for each day of serial multiple days in chronological order form a series of inter-day daily means, not necessarily consecutive.

"Chronic BG" (cBG) is the diabetic persistent level of BG as evaluated by a weighted time average over an extended period of multiple days, typically spanning multiple weeks. This is equivalent to the average of the CGM daily means over the same set of days.

The "intraday BG levels" are device readings of BG at specific times during the day, typically specified by self-monitoring-blood-glucose (SMBG) protocol or CGM sampling rates. These intraday BG levels spanning multiple days in chronological order form a summary series of daily BG events. Patients use the SMBG-protocol when measuring their BG level by skin stick pens of metering devices. The typical seven SMBG-defined events are before and after breakfast, before and after lunch, before and after dinner, and bedtime, and sometimes augmented by before and after snacks.

An "inter-day diabetes state" space is defined by the day-to-day (inter-day) dynamics of BG daily means, specific intraday events, and other daily metrics.

"Phase plots" or "phase portraits" are the time patterns of data points created by the serial values of inter-day state-space variables as coordinates.

"Time patterns" form an ordered structured (deterministic) flow known as an "orbit" according to the geometry of an attractor basin. The "attractor basin" is defined by all possible orbits whose initial phase point is in the attractor basin. The attractor basin for inter-day daily mean is distant from the attractor basin of another inter-day metric by a "vector constant", specific to each patient, which slowly changes over a year. Inter-day metrics are derived from intraday readings. References by the popular term "daily" are ambiguous.

The "International Diabetes Center" (IDC), located at Park Nicollet International Diabetes Center, 3800 Park Nicollet Blvd., St. Louis Park, MN, and founded by Donnell D. Etzwiler, MD, in 1967, provides world-class diabetes care, education, publications and research that meet the needs of people with diabetes and their families.

"Acute glycemia" is defined as hypoglycemia for recurrent extreme low BG levels typically <71 mg/dL and/or hyperglycemia for recurrent extreme high levels typically BG>249 mg/dL.

"Receiver operating characteristic" (ROC) plots correct predictions (true positives) versus error predictions (false positives) as the decision threshold of the prediction method (process) varies over its defined scale.

"Area-under-the-curve" (AUC) is the integrated area under the ROC plot and scales from 0 (100% mis-classification) to 1 (100% correct).

"Sync function" is a simple combination of specific intraday BG readings that monitors A1C-related chronic BG with high accuracy.

"An acute-glycemia day is defined as "recurrent hypoglycemia" or "persistent hypoglycemia" or "recurrent hyperglycemia" or "persistent hyperglycemeia" for a specified percentage of 24 hours, typically about 2%.

The "approximate glycemic average/mean" of any daily variable X from day d back to day d−k+1 of a study is defined as:

$$X_{Adk} = \frac{1}{N} \sum_{n=0}^{min[d,k]-1} X_{d-n}, \tag{1}$$

where N is the count of monitored days in the k-day span. The kinetics and lifespan of glycated red cells imply k equals ~90 days, as used in the present invention. Setting k to other values, e.g., k<90, detects faster features such as changes in relative position between orbits.

The "exact glycemic weighted average/mean" of any specified daily metric X from day d−k+1 up through day d is defined as:

$$X_{Adk} = \frac{1}{N} \sum_{n=0}^{min[d,k]-1} X_{d-n} * W_{d-n}, \tag{2}$$

where N is the sum of weights of monitored days (md) in the k-day span, and where $$N = \sum_{n=0}^{min[d,k]-1} W_{d-n} \tag{3}$$

where Wd−n>0 weights the historical impact of aging glycated red cells. Hence, recent glycations have more impact than older HbA1C cells. $W_d$ is designed in accordance with the relative importance of glycation history. Consequently, BG levels from the most recent 30 days have been shown to contribute approximately 50% to HbA1c, whereas those from the period 30-90 days and 90-120 days earlier contribute approximately 40% and 10%, respectively. Hence, the slow kinetics and lifespan of glycated red cells imply k approximates ~90 to 120 days, but the last 30 days have little impact while the first 90 has essentially major and uniform impact as expressed in the definition for "approximate glycemic average/mean". Setting k to other values, e.g., k<90, detects other features such as faster changes in the properties of orbits.

Modification of glycemic average: the glycemic average is assigned as missing values when (monitored days) md<3 in equation (2). When md=3, the average is calculated and inserted into all 3 prior md designations.

Reducing transients in initial (start-up) values of the glycemic average: when initial md values cover at least one cycle according to the present invention, the glycemic average (orbit centroid) is calculated and inserted into all prior initial start-up values of the average. Optionally, additional smoothing is achieved by applying the glycemic average equation (2) twice to the initial sequence of values.

A "Lorenz" variable pair is a dynamic variable and its embedded (time-delayed) version and is useful for analysis and analytics of a dynamic state space.

"Logistic regression" relates observed factors to the probability of defined events/classes.

"Contingency tables" or "truth tables" report classification performance in terms of correct and incorrect calls.

A "profiler" graphs the impact of known factors on the probability of defined events/classes.

DETAILED DESCRIPTION

Referring now descriptively to the drawings and definitions, the attached figures illustrate the nonlinear dynamic basis, geometry, and clinical application of the present invention for predicting acute glycemia. FIGS. 1 to 26 illustrate the state-space attractor orbit properties, statistical analyses, and information systems supporting the New Diagnostic that predicts acute glycemia. All statistical analyses and contingency tables are standard methods performed and described by JMP® 8.0.2 provided by SAS Institute Inc., located at SAS Campus Drive, Cary, NC, USA 27513.

Described herein are processes and systems useful in predicting impending acute diabetic glycemia based on both intraday distributions of blood glucose (BG) readings and intraday BG summary metrics using their inter-day geometrical patterns.

Recurrent extreme levels of blood glucose (BG) during any day lead to serious health complications as well as dangerous challenges to survival. The intraday distribution of BG can be divided into population quantiles Q %. For example Q10% is the BG level capturing the first (lower) 10% of intraday BG readings. Hence, the intraday recurrence time of BG levels at or below Q10% is approximately 0.10×24 hours. Extreme population levels are captured by extreme quantiles. We select Q02% to monitor potential hypoglycemic episodes and Q98% for potential hyperglycemic episodes. Both of these hypoglycemic episodes and hyperglycemic episodes quantiles are classified as acute glycemia. Conversely, one could monitor the quantile level of critical BG values, such as BG=250 for hyperglycemia and BG=70 for hypoglycemia.

Intraday populations are collected by CGM devices or SMBG profiles. The sampling rates of CGM devices are obviously superior to SMBG events, but currently the SMBG protocol is much more prevalent among patients. CGM data provide quantiles directly.

Approximation of quantile (Q) values from SMBG profiles requires two steps: (1) a normalizing transformation of BG readings; and (2) use the normal approximation to calculate quantiles. Many methods are available for step 1. In one example, the Ln transformation, $\log_b(BG)$, where the base b can be any value, typically "e". Then in step 2, a mean value "m" and standard deviation value "s" of the Ln values are calculated. The Q02% and Q98% quantiles are estimated as m−2.08 s and m+2.08 s respectively. FIG. 1 shows that both data sources provide similar though not identical quantile information, with the SMBG data values 10 for the Q02% quantile being shown in FIG. 1A and the CGM data values 12 for the Q02% quantile being shown in FIG. 1B.

Figure 2:
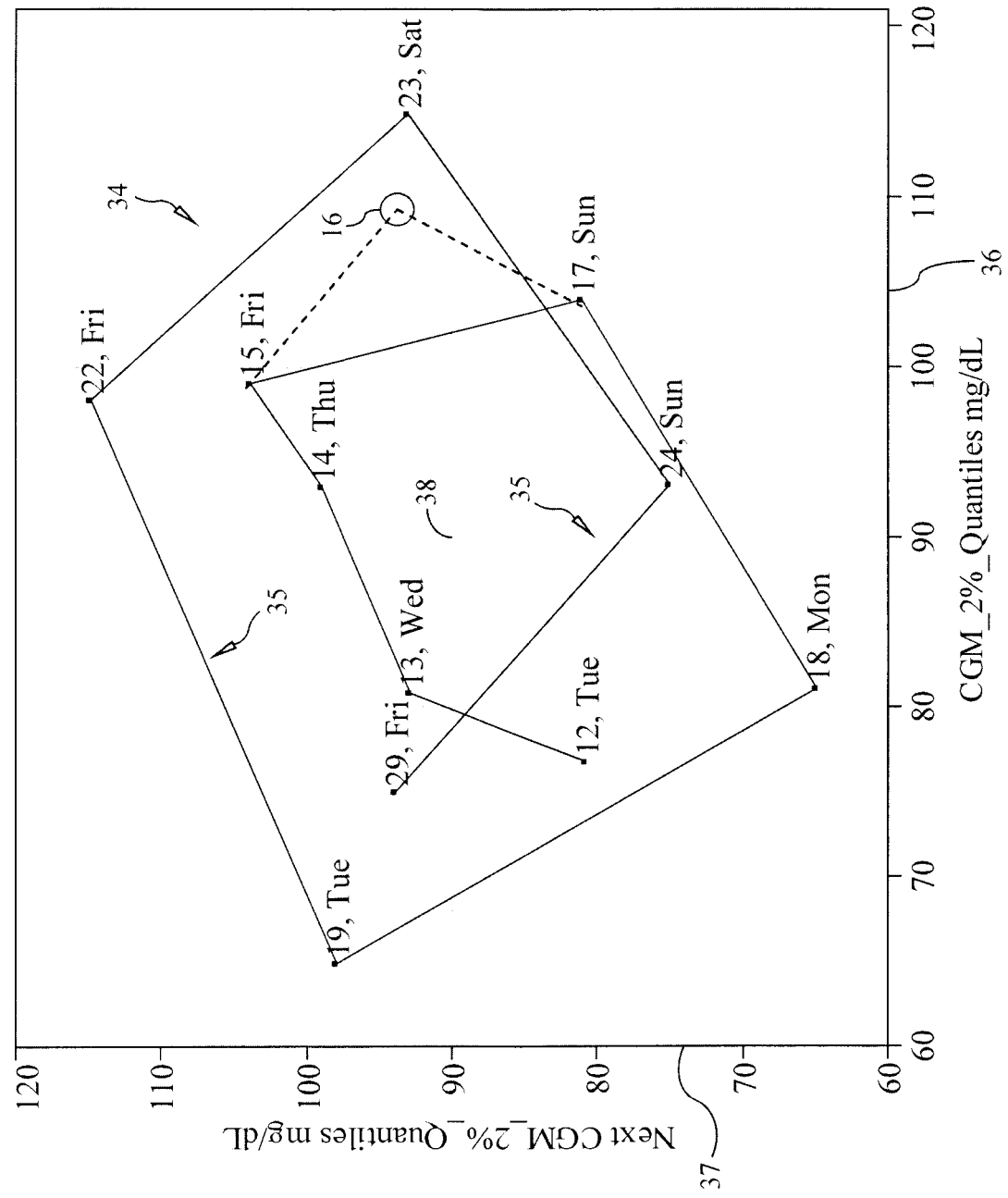
FIG. 2 is a Lorenz dynamic flow map for 2% Quantiles of intraday CGM readings, according to an embodiment of the present invention.

FIG. 2 is a Lorenz phase plot 34 of 2% quantile BG readings (Q02%), future versus prior, that shows the inter-day orbits and geometry that support the present invention. Typical inter-day phase-portrait patterns for 2% quantiles (Q02) of intraday CGM distributions as shown are synchronized with other inter-day BG metrics such as the intraday fasting BG levels (FB) that were described in detail in co-pending application Ser. No. 13/895,054, filed May 15, 2013, which is hereby incorporated herein, in its entirety, by reference thereto. The ordered flow patterns (orbits) described in the definitions are characteristic of the deterministic phase dimensions discovered by the prior application Ser. No. 13/895,054. These phase portraits are contained within the circular/ellipsoidal attractor-basin geometry of the diabetes inter-day state space discovered in the prior invention. The diameter of these orbits reflects the degree of inter-day metric fluctuations (scatter). According to the statistical principle of variance composition described as "analysis of variance" (ANOVA), these inter-day variations contain and represent an upper bound for the intraday fluctuations.

The orbits 35 are the consequence of the endocrine system attempting control of BG facing the challenge of diabetes, by analogy similar to the planetary orbits created by gravity. Orbit-point labels (e.g., see 12, 13, 14, 15, 17, 18, 19, 22-24, and 29 in FIG. 2) indicate monitored days (mdays) in chronological order as distributed over a fixed interval of time. The Lorenz pair now-day quantile is located by the horizontal X axis 36 and next-day quantile is on a vertical Y-axis 37 grid. Note in FIG. 2 the orbits 35 flow about the attractor centroid 38, approximated as (90, 90) mg/dL. Hence, the initial day 12 in the diagram locates as vector coordinates near (X=80, Y=80), and the orbit continues as a series of plotted vectors (X, Y) to day 29, Friday. Note a complete 360-degree non-closed orbit 35 cycle requires typically 6 to 8 days. There is a background of significant statistical noise occasionally injecting sharp-angled disruptions. Some days may be missing (for example, empty circle 16 in FIG. 2) in the sequence but the orbit structure is evident. As in the prior invention, the orbits flow clockwise with the occasional interruptions (noise blips). Depending on the magnitude-location of the attractor centroid 38, low next-day values can imply acute glycemia. Hence, relative to the centroid 38, point 17 would predict a hypoglycemic next day, as verified by day 18. Therefore, one can graphically monitor BG trends for acute alerts using CGM or SMBG intraday data.

Thus, a user, when viewing the plot 34 of FIG. 2 can readily identify that the person being monitored had acute hypoglycemia (blood glucose (BG) value of less than 70 mg/dl) for at least 28 minutes on day 18, Monday (2% of 24 hours is 28 minutes). By graphing different quantiles (e.g., Q01, Q04, or any other preselected quantile), it can likewise be determined when a patient has acute hypo or hypoglycemia for at least the amount of time represented by each respective quantile. Note that the Q98 quantile would show days that a patient experienced acute hyperglycemia for at least 28 minutes on any particular day.

The labels also contain lifestyle information in terms of work day versus free days (weekend). Consequentially, FIG. 2 indicates for this subject that the weekend lifestyle increases his/her hypoglycemic risks.

Figure 3:
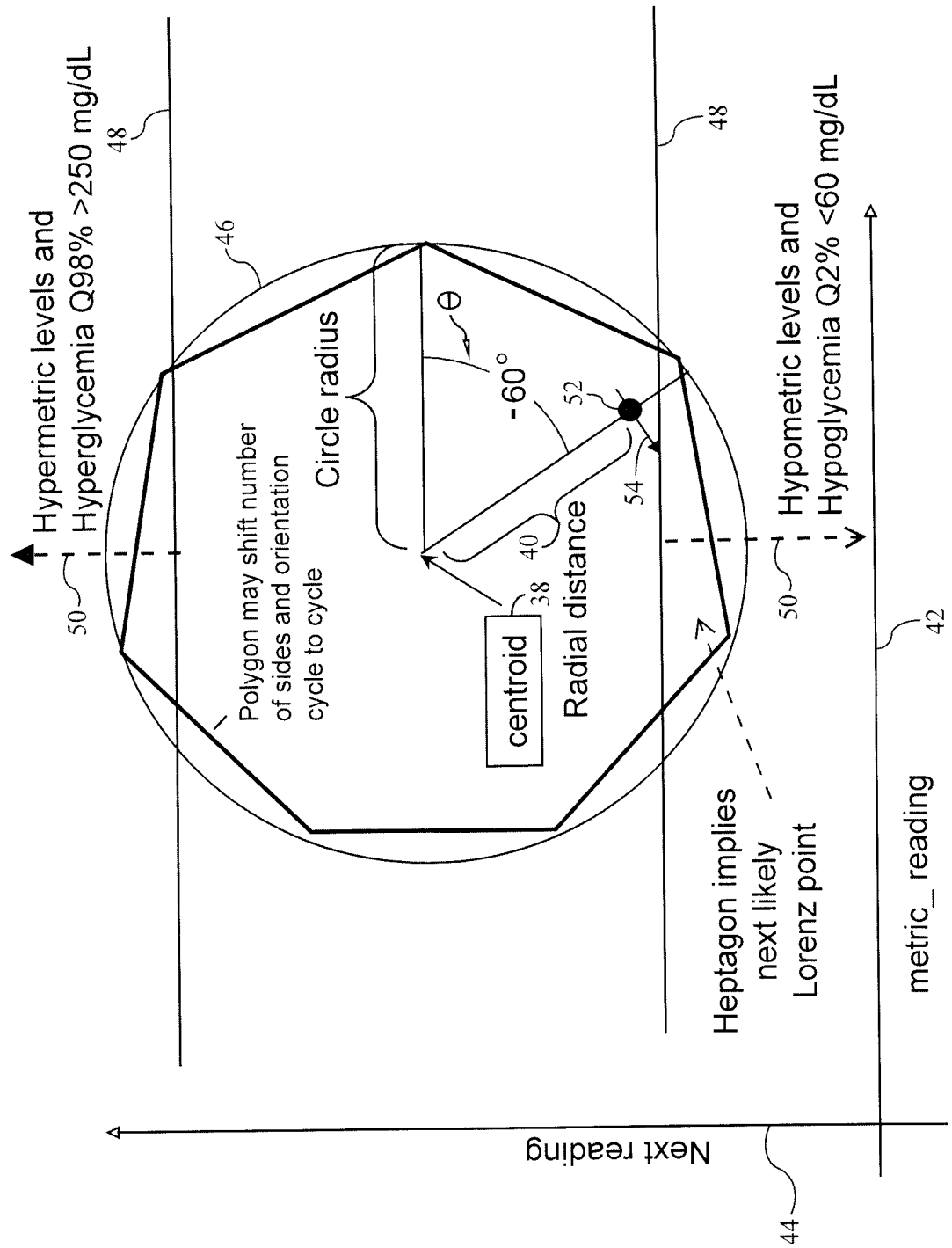
FIG. 3 shows a diagram of Lorenz geometry invented for a diagnostic that predicts acute glycemia, according to an embodiment of the present invention.

FIG. 3 diagrams the basin geometry of the attractor indicating its centroid 38 (center of attraction) and radius 40. The horizontal X-axis 42 is the current-day axis while vertical Y-axis 44 is the next-day axis. The large circle represents the attractor region 46 as centered on its trending centroid 38. The solid horizontal lines 48 represent acute glycemia thresholds. The two dotted next-day vectors 50 indicate the hypoglycemic/hyperglycemic directions. The small solid dot 52 is a typical orbital point indicating the next point in the flow direction of the small arrow 54.

Negative angular flow is clockwise rotation. Since 7 days is a typical complete cycle, the angular increment is ~−52 degrees (−360/7) on average. Hence, in the diagram the next-day orbital point relative to current-day angle at −60° from horizontal will likely be in the hypoglycemic zone. Note this diagram can shift in centroid location and size over time due to potential trending of the centroid 38 and/or radius 40.

Figure 4:
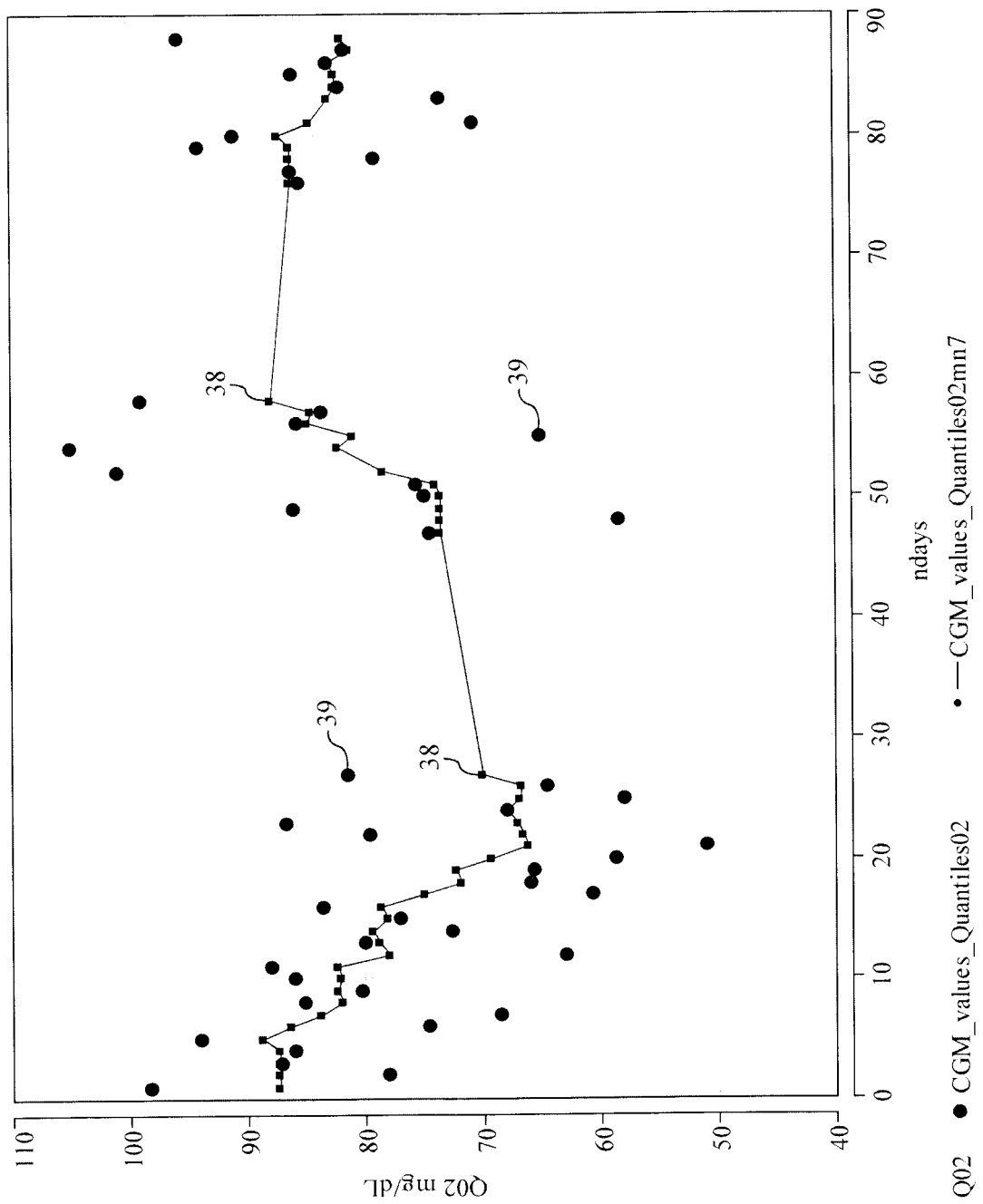
FIG. 4 illustrates an example of centroid tracking according to an embodiment of the present invention.

FIG. 4 illustrates tracking of the shifting of centroid location over time (centroid tracking-small squares) using the algorithms defined above with regard to approximate glycemic average/mean, exact glycemic weighted average/mean and modification of glycemic average defined above, with k set to 6 to cover 7 days typical of complete cycles. The Q02 values are shown as the large circles 39 and the centroid values are shown as the small squares 38. Hence, the centroid 38 is updated over complete weekly cycles. The centered Lorenz variables in FIG. 5, CGMQ02, are data vectors minus their trending centroids. Hence, they are plotted relative to stationary (0,0) coordinates, avoiding the complexity of trending centroids, thereby de-trending the data. Hence, they plot all combinations of Q02 relative to their respective centroids. The larger sized dots 41 flag Q02<=60 relative to centroids >=70, which is an alert condition. Similarly, FIG. 6 indicates hyperglycemic Lorenz pairs as big dots 41.

Figure 5:
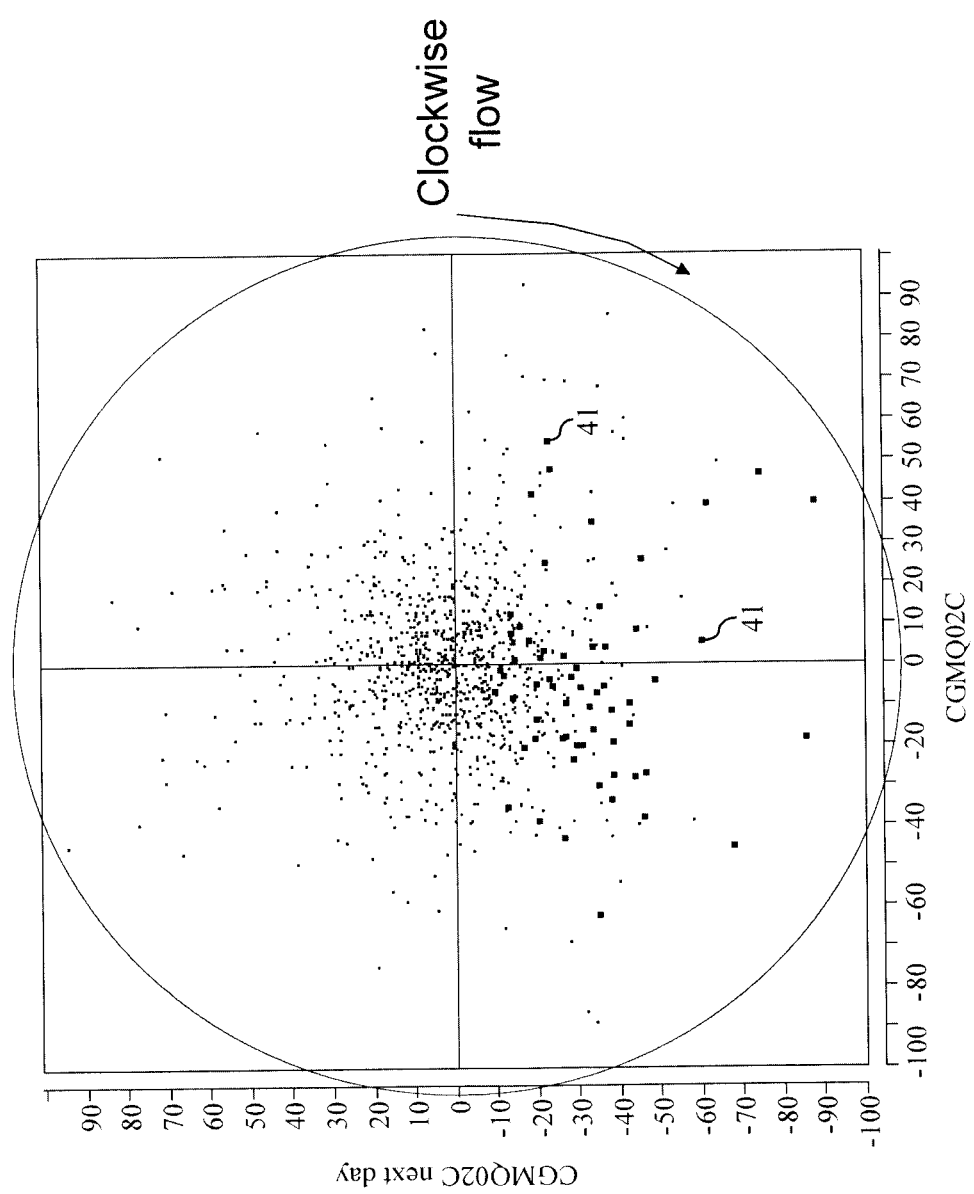
FIG. 5 illustrates Lorenz dynamic flow geometry for Q02 according to an embodiment of the present invention.
Figure 6:
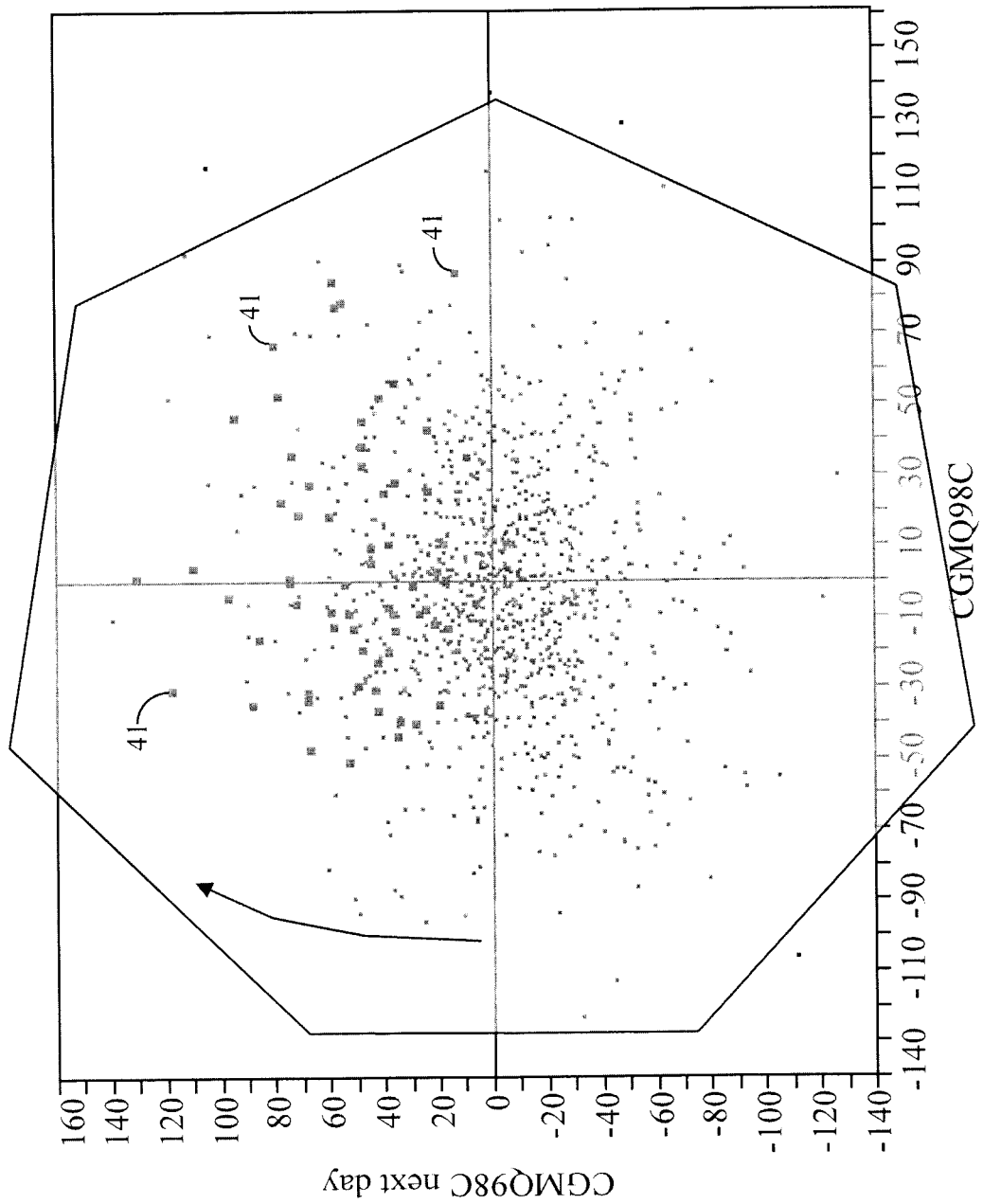
FIG. 6 illustrates Lorenz dynamic flow geometry for Q98 according to an embodiment of the present invention.

Proper tracking and de-trending enables one to apply graphical methods to the Lorenz Map 34 of FIG. 2 and basin template of FIG. 3 to predict impending acute glycemia. FIGS. 5 and 6 illustrate how the deterministic Lorenz flow enables these next-day predictions of impending episodes of extreme BG levels. Applying the inter-day synchronized-chaos property of the intraday summaries, one may use any metric such as fasting BG (FB) to construct these plots, reducing the burden of comprehensive intraday profiling to a few strategic days. When fasting blood glucose (FB) are used, readings for these values are typically taken once per day, before breakfast. Hence, when the FB orbits approach critical zones near the coordinate axes, a CGM device or comprehensive SMBG strategy can be initiated to evaluate the BG quantiles, such as Q02% near the right horizontal axis or Q98% near the left horizontal axis. Using the FB angle ($\theta$) (see FIG. 3, for an example of metric angle $\theta$). which is the metric to approximate the Lorenz Q-angle (an example of which is shown as angle $\theta$ for a heptagon in FIG. 3), one estimates the Q-centroid (denoted $C_Q$) by $$C_Q=(\sin(\theta)Q_{now}+\cos(\theta)Q_{next})/\cos(\theta)+\sin(\theta)), \quad (4)$$

where Q can be either Q98% or Q02%. This enables both graphical and intuitive prediction of next-day Q levels using the combined metrics of both FB and full-profile metrics. The centroid tracking formula (4) can be used to track the centroid of any metric used. The angles in the orbital positions of any metric plotted about their centroids tend to show increasing risk of extreme acute glycemia (including acute hypoglycemia and hyperglycemia) with increases counterclockwise rotation of the metric value from the horizontal axis (FIG. 5).

Figure 7A:
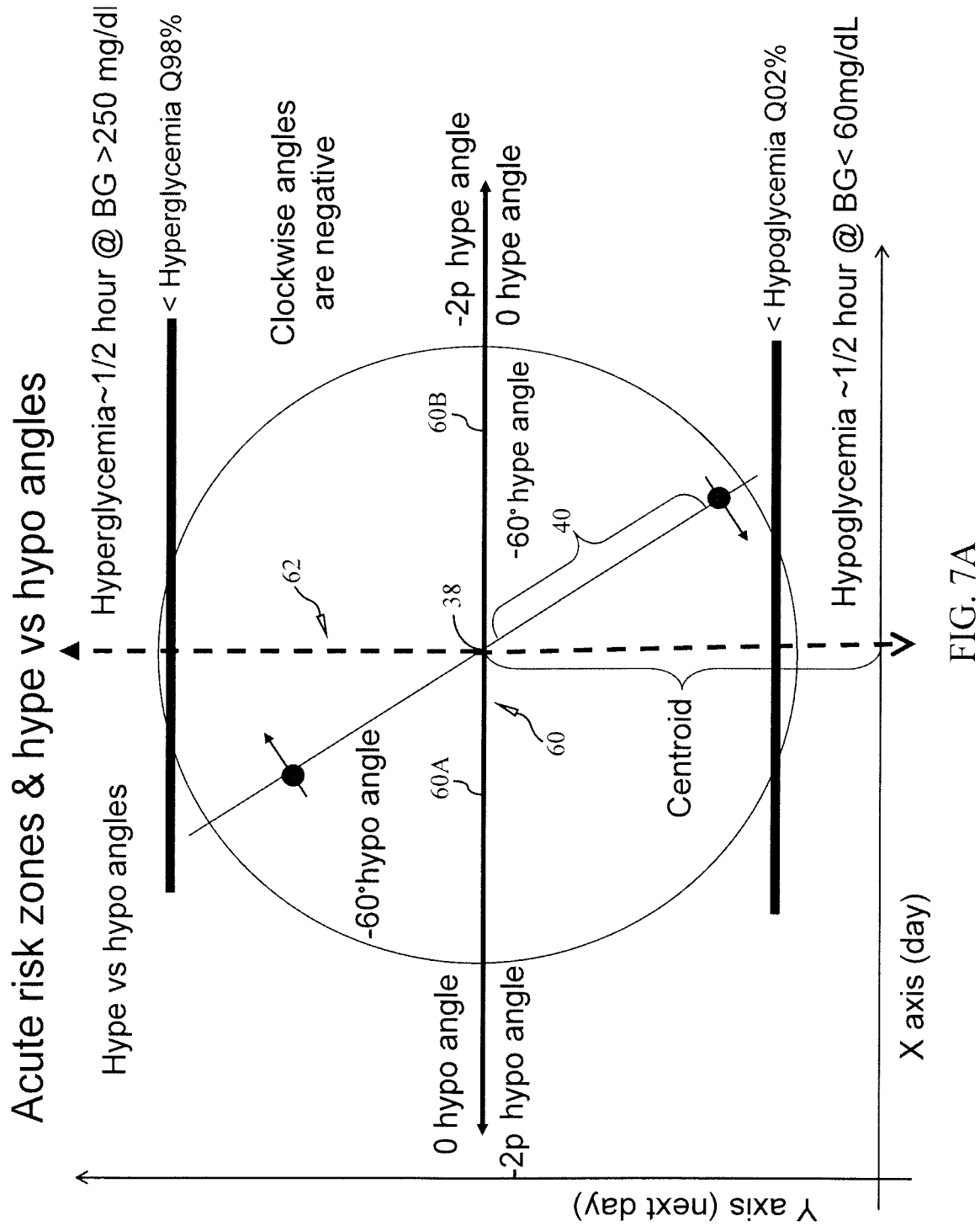
FIG. 7A-7B illustrate Lorenz dynamic flow geometry for predicting acute glycemia, according to an embodiment of the present invention.
Figure 7B:
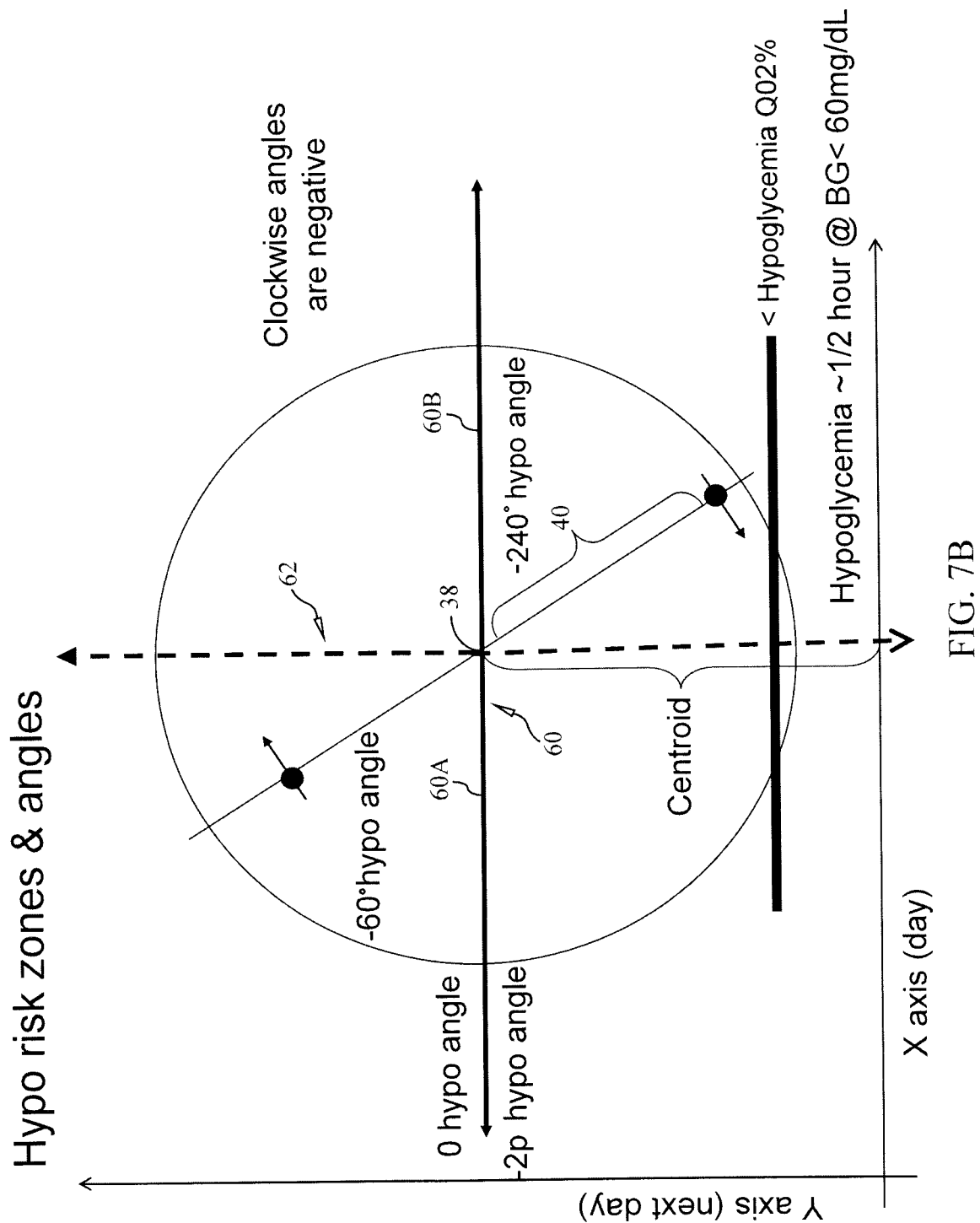
Figure 10:
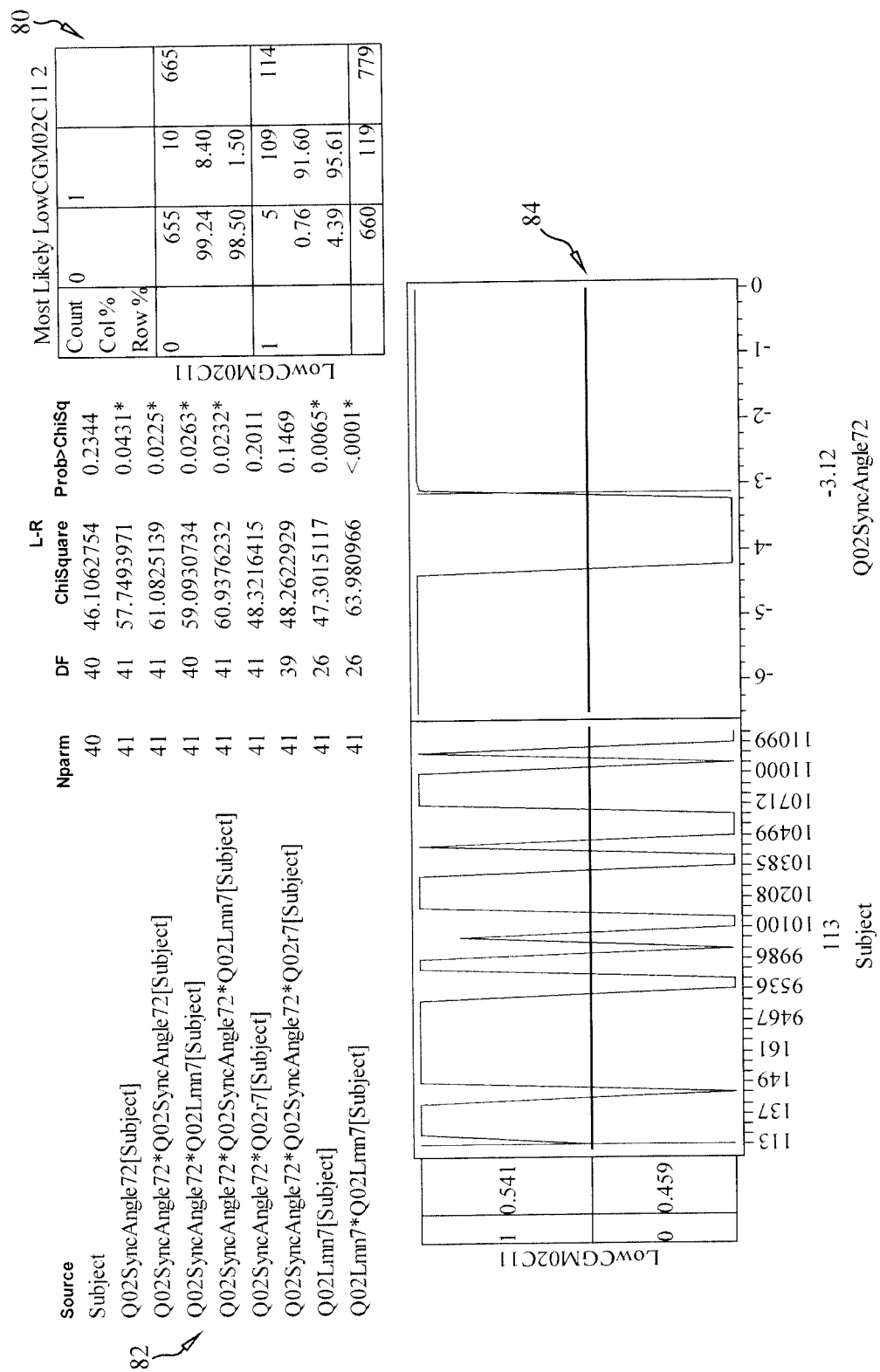
FIG. 10 shows results from using Q02 data to predict next-day acute glycemia risk Q2%, according to an embodiment of the present invention.
Figure 11:
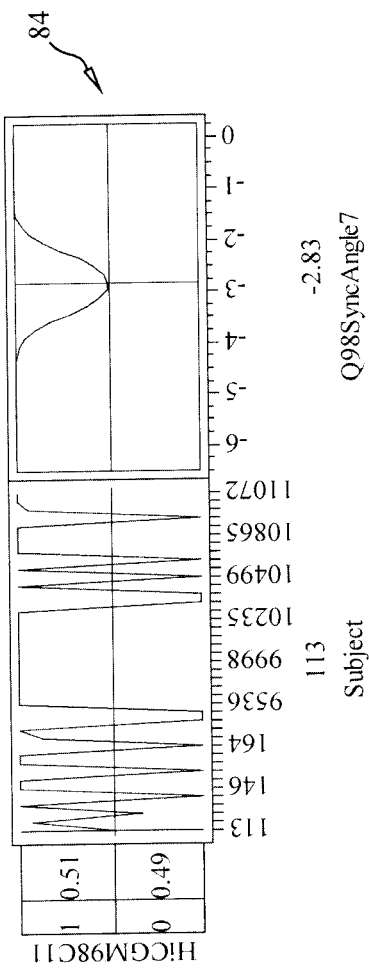
FIG. 11 shows results from using Q98 to predict next-day acute glycemia risk Q98%.
Figure 12:
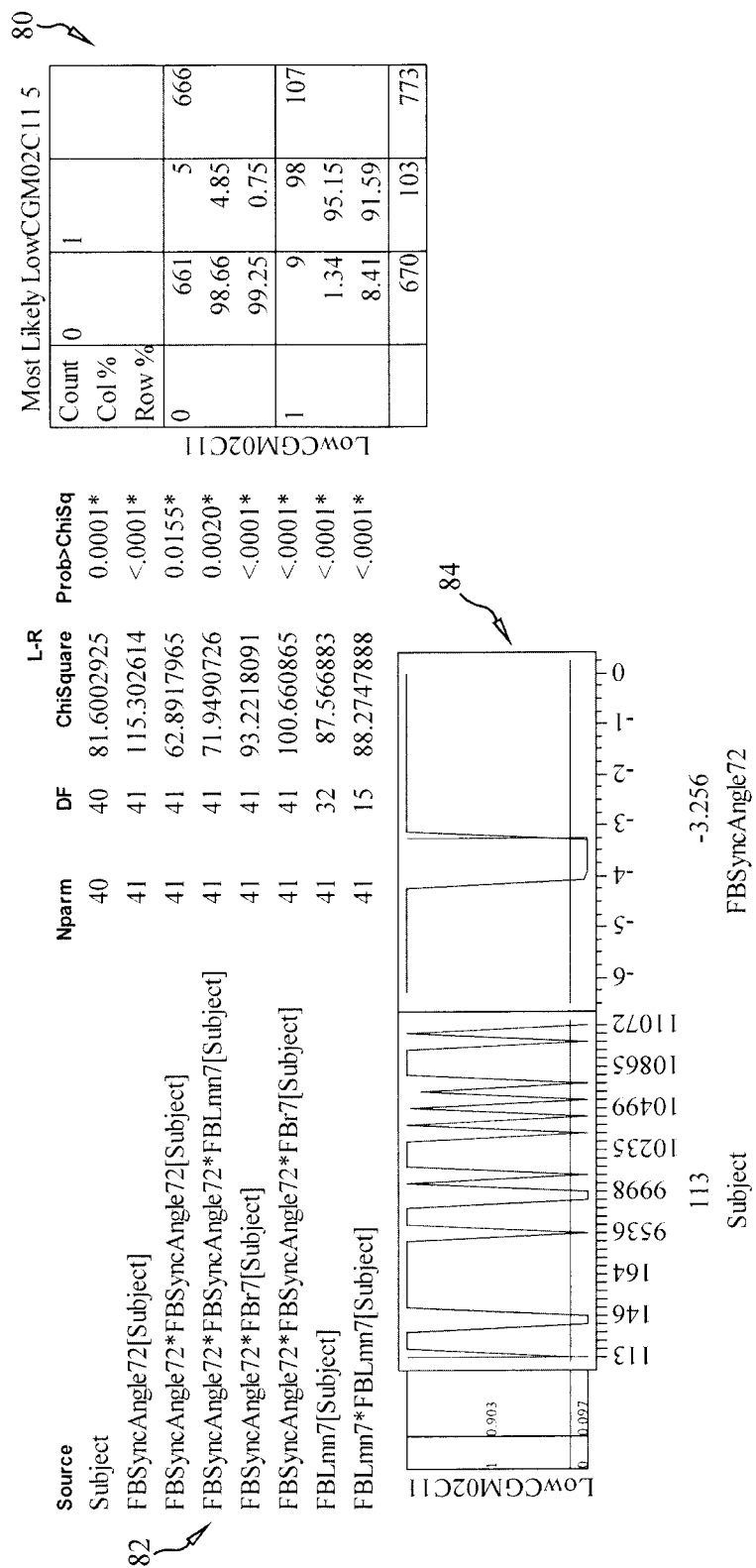
FIG. 12 a fast blood glucose (FB) model for predicting next day Q02 acute glycemia risk, according to an embodiment of the present invention.
Figure 13:
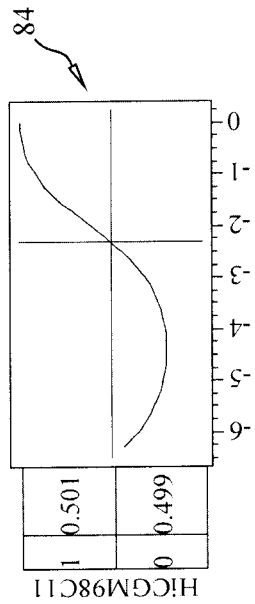
FIG. 13 a fast blood glucose (FB) model for predicting next day Q02 acute glycemia risk, according to an embodiment of the present invention.

Quantitative monitoring of acute quantiles requires models that represent probability trends over the deterministic evolution of multiple dynamic variables. One such model uses logistic regression based on functions of Lorenz factors as illustrated in FIGS. 7A and 7B. FIG. 7A overlays both hypo and hyper diagrams, while 7B splits out the hypo diagram. Logistic regression is well known in the statistics literature. Particularly, JMP*SAS 8.0.2 is an excellent reference. Nominal logistic regression relates probabilities of nominal classifications to known factors. Accordingly, logistic regression fits the Ln probability of acute glycemia in terms of a model of these multiple factors. A probability >50% for extreme quantiles at any Lorenz phase point is identified as an extreme glycemic day. If the quantiles surpass clinical threshold limits, then the classification becomes acute glycemia. Any summary BG metric and model may be used. In one embodiment, a simple, parsimonious linear model is used for next-day probabilities of quantile levels using functions of factors that locate the attractor centroid and vector position within the attractor basin of active dynamic variables in terms of Lorenz coordinates (as defined above), e.g., functions of trending centroids 38, radial distance 40, and hypo/hyper angular positions respectively. Consider function version $\cos(\theta+\delta)$, where theta is the Lorenz angle relative to defined references in FIG. 3 and delta shifts the max/min locations of the cosine function away from 0 and pi. Delta is optimized by nonlinear fit to the data. This function will maximize at $\theta+\delta=0$ and minimize at $\theta+\delta=\pm\pi$, and can be expressed linearly as a $\cos(\theta)+b\sin(\theta)$, where $\delta=\arc\tan(-b/a)$. Note b and a can contain linear functions of factors independent of $\theta$. The a/b function version is optimized by linear regression. Similarly, another linear representation is a quadratic polynomial of $\theta$, which has a maximum zone and a minimum zone with discontinuity at $\pm 2\pi$ radians. This polynomial can also interact with other factors and is optimized also by linear logistic regression FIGS. 8 and 9 introduce both the Lorenz Response Surface (LRS-polynomial) and Design of Experiment (DOX) methods.

A logistic Lorenz Response Surface can be defined as:

$$\text{Prob of extreme } Q\text{-levels}=\exp(1inf) \quad (5),$$

where 1inf is a linear combination of any of the following 11 polynomial Lorenz factors:
1. :M0~:Subject (impact of subject differences),
2. :metric_Angle (angle of metric),
3. :metric_Angle*:metric_Angle (angle of metric)$^2$,
4. :metric_Angle*:metric_LC (centroid impact on angle),
5. :metric_Angle*:metric_Angle*:metric_LC (centroid impact on angle$^2$),
6. :metric_Angle*:metric_Lr (radial distance impact on angle),
7. :metric_Angle*:metric_Angle*:metric_Lr (radial impact on angle$^2$),
8. :metric_Lr (radial impact),
9. :metric_Lr*:metric_Lr,
10. :metric_LC (centroid impact),
11. :metric_LC*:metric_LC For example for metric FB, metric_LC becomes FB_LC.

For each Lorenz point and any BG inter-day metric: M0 is a constant, Angle is its clockwise angle, LC is the Ln Centroid, and Lr is the Ln radial distance r. The radial distance r may also be used directly. C is denoted mn7 in the specific models; and ":" indicates a logistic regression variable. Appending [:Subject] to a factor indicates subject differences of factor impact.

Angles are defined with respect to a detrended metric using k=6 in the equations (1) and (2) above. The clockwise angle is negative from either the left (hypo) or right (hype) horizontal axis 60, depending on model target for acute risk. To minimize impact of polynomial discontinuity at complete ($2\pi$(radians)) rotations, the left horizontal axis 60A is the zero-angle reference for hypoglycemia and the right horizontal axis 60B is the reference for hyperglycemia, as illustrated in FIG. 7. Hence, to predict next-day extreme quantiles, the earliest effective test zone is expected to be in general at $-\pi$(radians). However, for subjects already in a severe risk condition this angle will be nearer to the vertical axis 62 located at $-\gamma/2$ radians.

The polynomial logistic model can be transformed to the Cos(angle+$\delta$) representation as follows:
- Replace "metric_Angle" with cosine(metric_Angle)
- Replace "metric_Angle*metric_Angle" with sine (metric_Angle)
- Recall, $A\cos(\theta+\delta)=a\cos(\theta)+b\sin(\theta)$, where $\tan(\delta)=-b/a$, $A^2=a^2+b^2$
- Note "a" and "b" can depend on any combination of factors independent of angle $\theta$.
- The LRS and Lorenz cosine models produce equivalent results.

Referring now to FIG. 8, a design of experiment (DOX) evaluation 70 is described according to an embodiment of the present invention. The data in FIG. 8 show that this linear function (LRS function that linearly combines up to 11 terms as described above are optimized by regression fit of the data) is effectively trained using at least 2 orbit cycles. Extreme Q levels are inherently in these cycles. Hence, using fitting concepts such as generalized least squares, the function can be tuned to predict the desired probabilities. JMP*SAS approximates this fitting process using logistic regression to model acute risk in terms of Lorenz factors.

Logistic regression tests all potential factors to fit the data. Angular functions are either trigonometric functions or polynomials. Using the SAS profiler, these regression functions identify important angles for next-day predictions. Cross terms of these functions with other factors identify how these important angles may shift with variation in these other factors.

The model is evaluated by predicting next-day extreme quantile BG levels in terms of truth/contingency tables and by the impact of Lorenz factors. Nominal logistic regression measures the impact of Lorenz factors by statistical significance and profiler analyses. The significance ("Prob>ChiSq"<<0.05) of the likelihood ration (L-R) evaluates the importance of each term in the model.

The G-efficiency score 72 of 79.90542 reflects that the precision of the model is very good, as the G-efficiency score is set to a scale of 0 to 100, where a 100 score is perfectly precise.

For all models predicting next-day glycemic metric levels, the prediction date must be within 2 or 3 days of the prior (predictor) date. 780 monitored days distributed over several months satisfied this restriction. For specific models missing parameter values can reduce this number to between 780 and 770. For special models, the number of days were reduced by design. The truth table, section (1) in FIG. 9, reveals the total of days used by each model. CGM provides readings every 5 or 10 minutes per day (typically 300 to 600 values per day). SMBG events typically are before and after meals and snacks as well as bedtime (typically 6 to 7 per day). For example fasting BG is before breakfast and is the most typical event among diabetes subjects.

Special FIG. 9 diagrams the tri-section analysis for all models showing: (1) truth table 80, (2) significant factors 82, and (3) profiler graph 84. The truth table 80 counts correct and incorrect model predictions. The significant factors 82 show the importance of model terms where prob>chisq is less than 0.05. The profiler graph 84) uses model profiles relating acute risk to Lorenz factors, typically the angle theta ($\theta$).

FIGS. 10 to 13 report tri-section evaluations using quantiles or fasting BG (FB) to predict next-day extreme acute quantiles. Using FIG. 9 template, All of the examples of FIGS. 10-13 show excellent model performance since, truth tables 80 indicate 90% correct predictions; and significant factors chart 82 shows that most of the terms are significant (important). The profiler charts 84 have a profile alert angle generally at about −3 radians for acute glycemia.

In order to reduce data burden and computational requirements, the present invention relies on the property of synchronized chaos (which states that all metrics tend to be at the same orbital angles over time) to combine FB angle monitoring with strategic quantile sampling. Hence, FB readings provide Lorenz angles. When near −3 radians patient should take distribution info, i.e., by CGM device or full SMBG profiles. The angle factors are calculated from FB readings. All other factors are calculated from distribution Q levels.

Figures 14A, 14B:
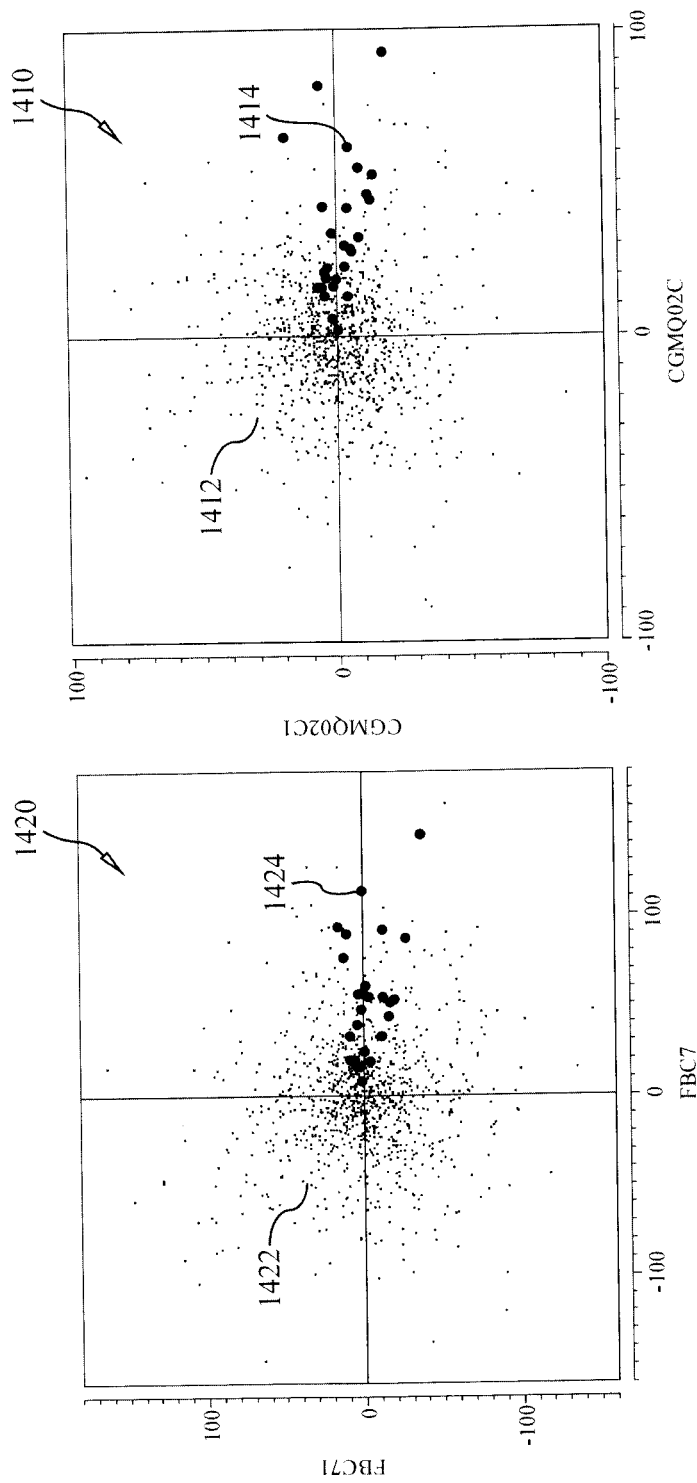
FIGS. 14A-14B show Lorenz data plots of synchronized chaos between Q02 and FB, according to an embodiment of the present invention.

FIGS. 14A-14B show Lorenz data plots of synchronized chaos between Q02 1410 and FB 1420, according to an embodiment of the present invention. Although not identical, it can be observed that the small dots 1412, 1422 show similar pattern placement. Likewise the large dots 1414, 1424 show similarities in location on the plots.

Figure 15:
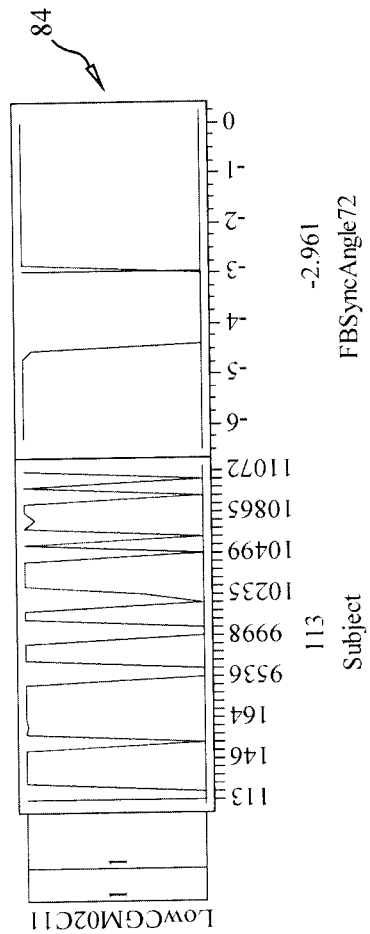
FIG. 15 illustrates an FBQ02 model using combined metrics to predict next day extreme Q02, according to an embodiment of the present invention.
Figure 16:
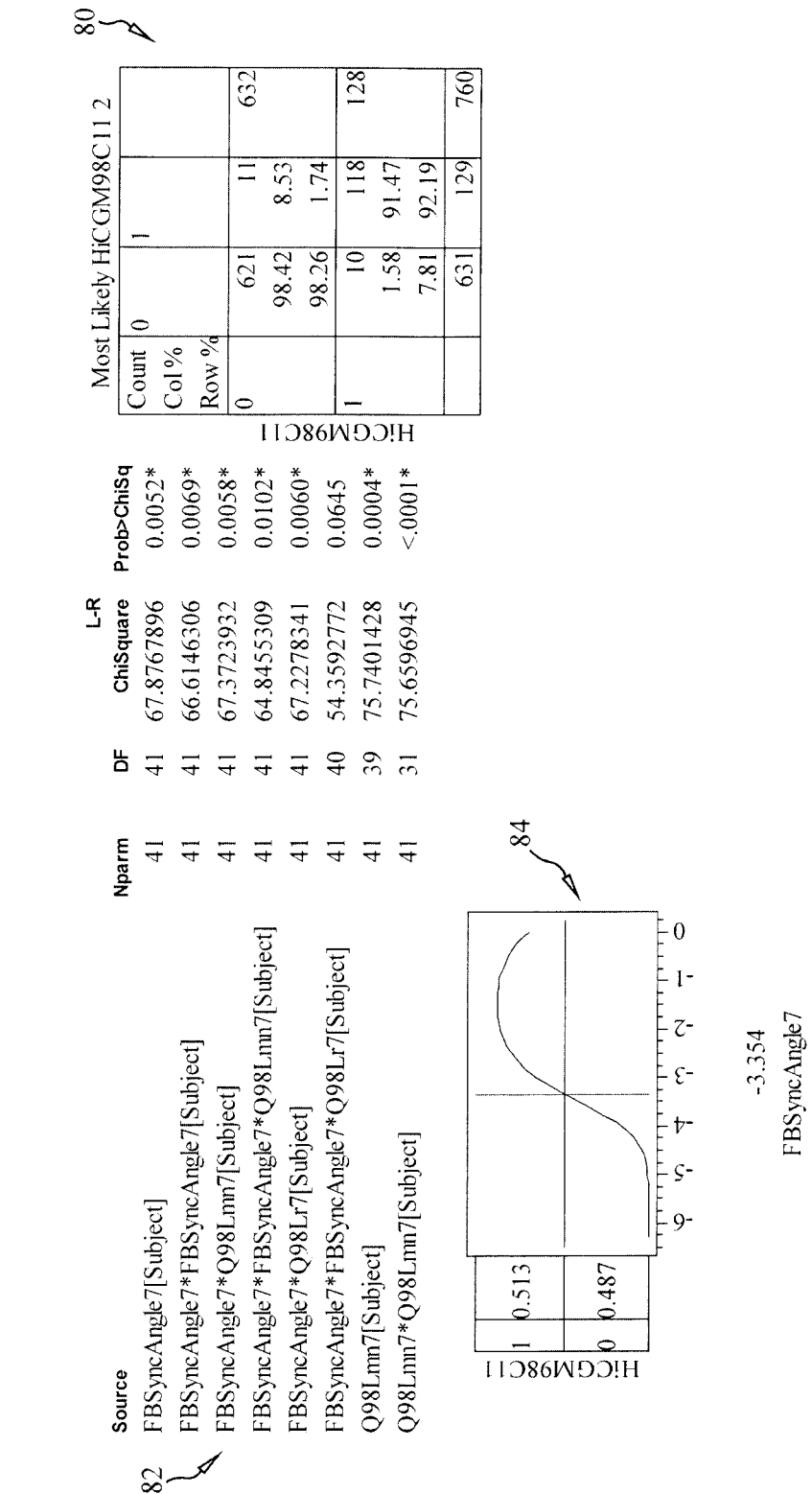
FIG. 16 illustrates an FBQ98 model using combined metrics to predict next day extreme Q98, according to an embodiment of the present invention.

FIGS. 15 and 16 report tri-section (80, 82, 84) evaluations using synchronized chaos to combine FB angle monitoring with strategic quantile sampling. Using FIG. 9, FIGS. 15 and 16 verify the success of this approach to predict next-day extreme quantiles, as all sections 1, 2, and 3 report very good results. Section 80 reports greater than 92% prediction success for 760 to 773 monitored days. Section 82 shows most Lorenz terms to highly significant, and section 84 supports the critical angle for predicting next-day glycemia to near minus three radians as expected.

Figure 17:
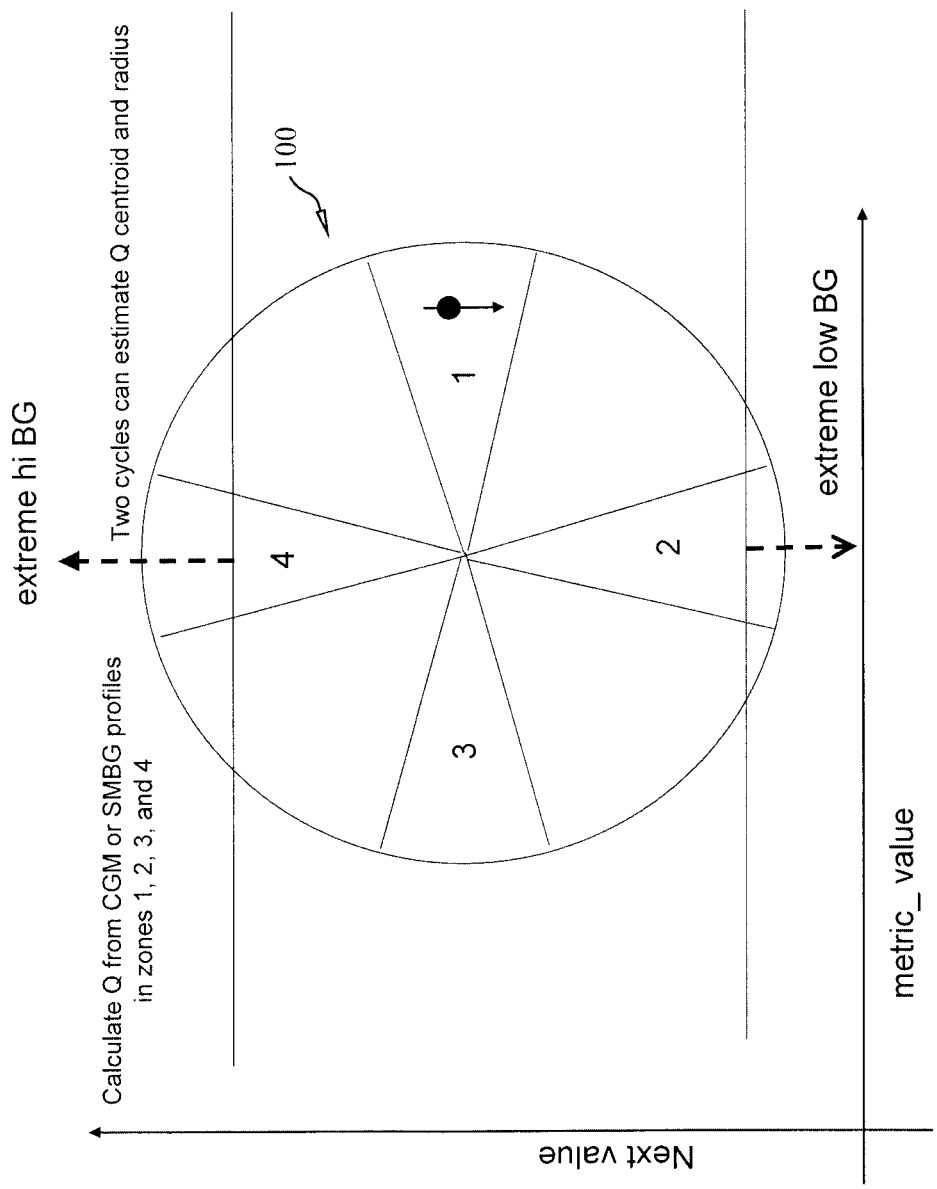
FIG. 17 shows a diagram of Lorenz dynamic flow geometry invented for low risk DOX to predict extreme BG levels, according to an embodiment of the present invention.

To reduce not only data burden but also model complexity and patient risks, FIG. 17 shows a strategy using extreme such as mild or moderate but not necessarily acute quantiles to train the model or graph-evaluator to be an alert system for acute glycemia. In general extreme non-acute Q levels would be Q02>60 and Q98<250 mg/dL. The diagram 100 applies to Q monitoring with focus on data near the axes. By template-definition FIGS. 18 to 21 evaluate this strategy and show that the training/alert combination steps work very well for Q02 and Q98 using models/graphs based on a single metric. The additional bar graphs show how well this special strategy extrapolates to predict serious acute events as an alert system. Note this result verifies the ability of the model to predict acute risk beyond the coverage of its (DOX) training data.

Figure 18:
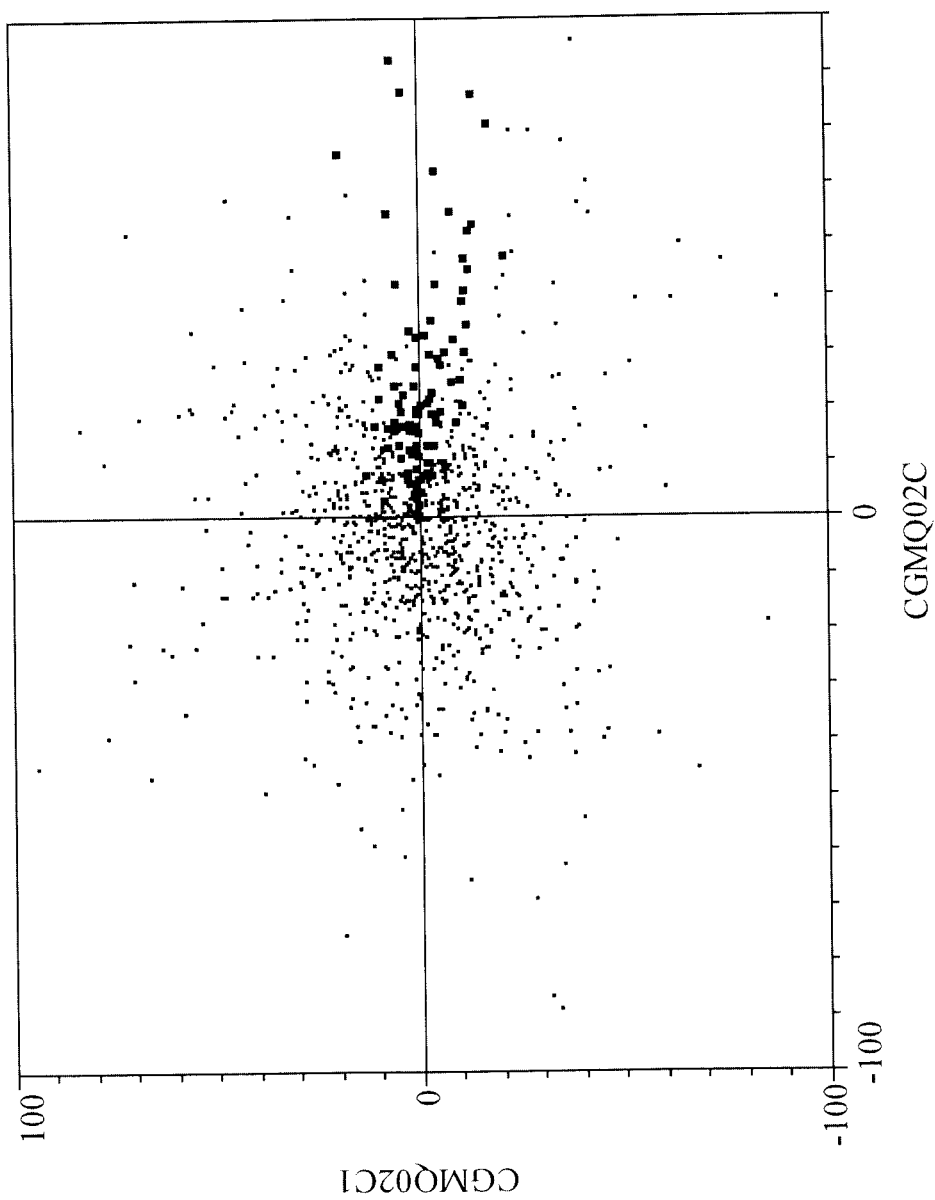
FIG. 18 shows low risk Q02 predictive data according to an embodiment of the present invention.
Figure 19:
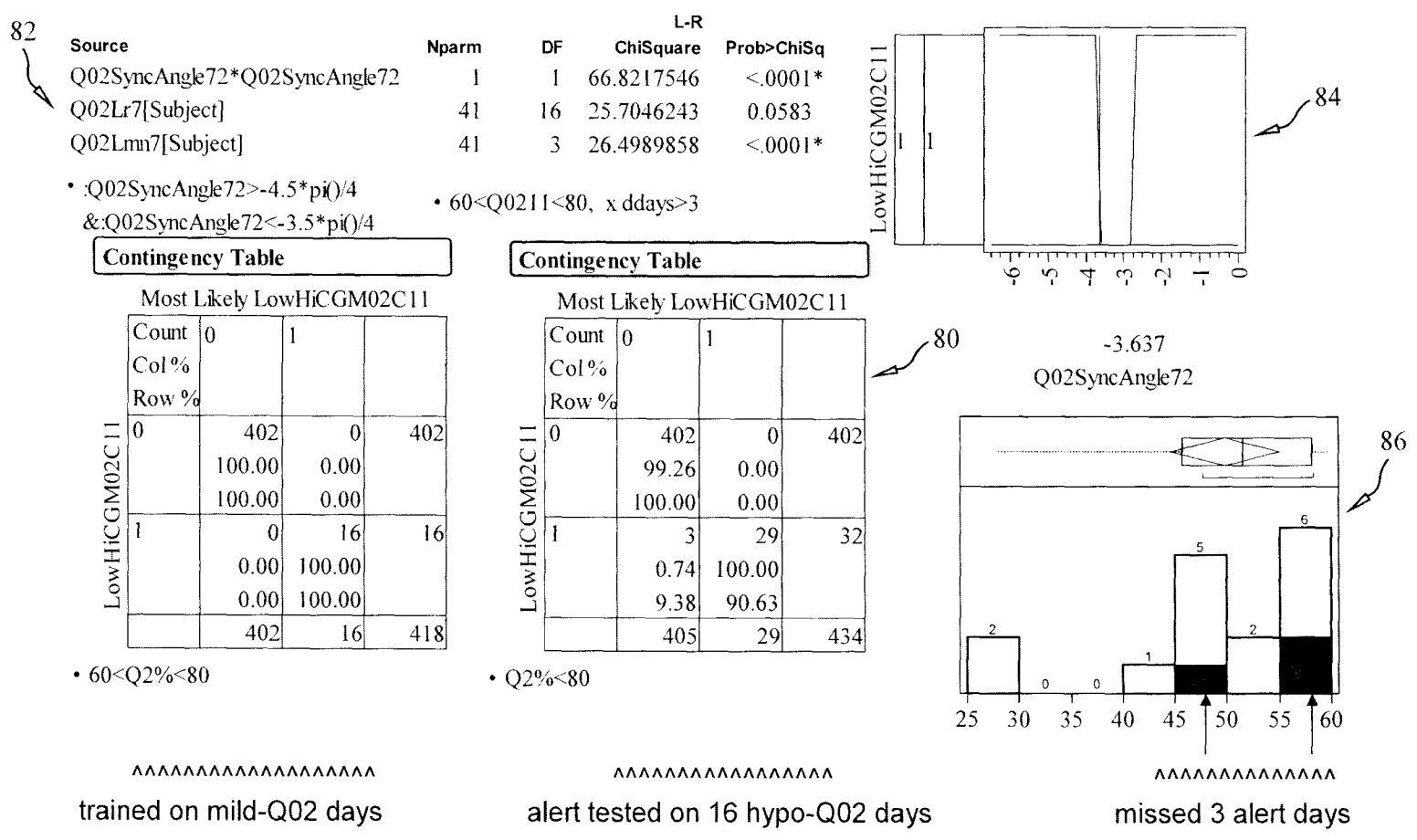

FIGS. 18 and 19 use Q02 distributions only near −3 radians (84) to predict next-day extreme low Q02 based on 418 days of Q02 data. The model requires only three significant terms to fit this restricted data (82) The truth tables (80) show perfect prediction for extreme lows and >90% correct predictions and alert extrapolations. The alert bar chart 86 shows the correct alerts and the three missed alerts (dark shades 87).

Figure 20:
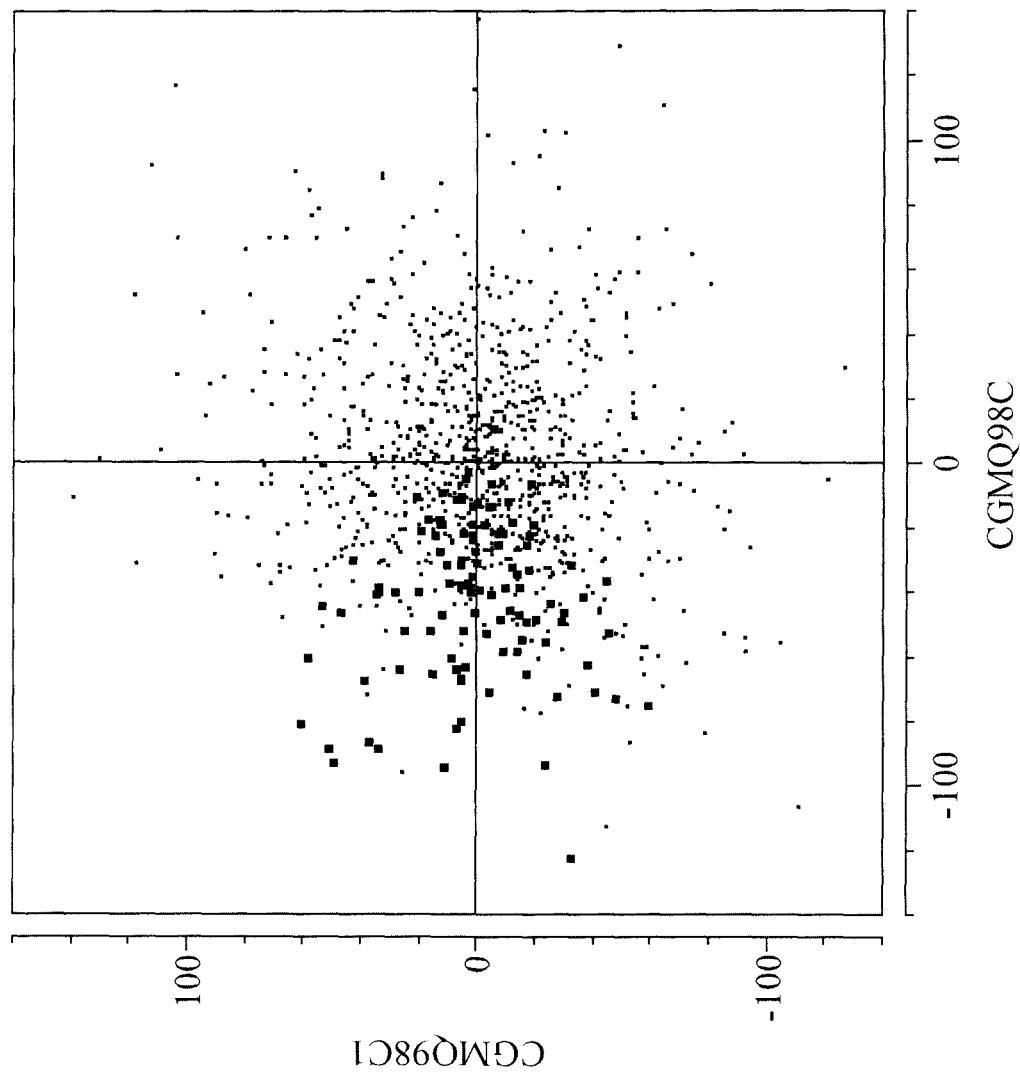
FIG. 20 shows low risk Q98 predictive data according to an embodiment of the present invention.
Figure 21:
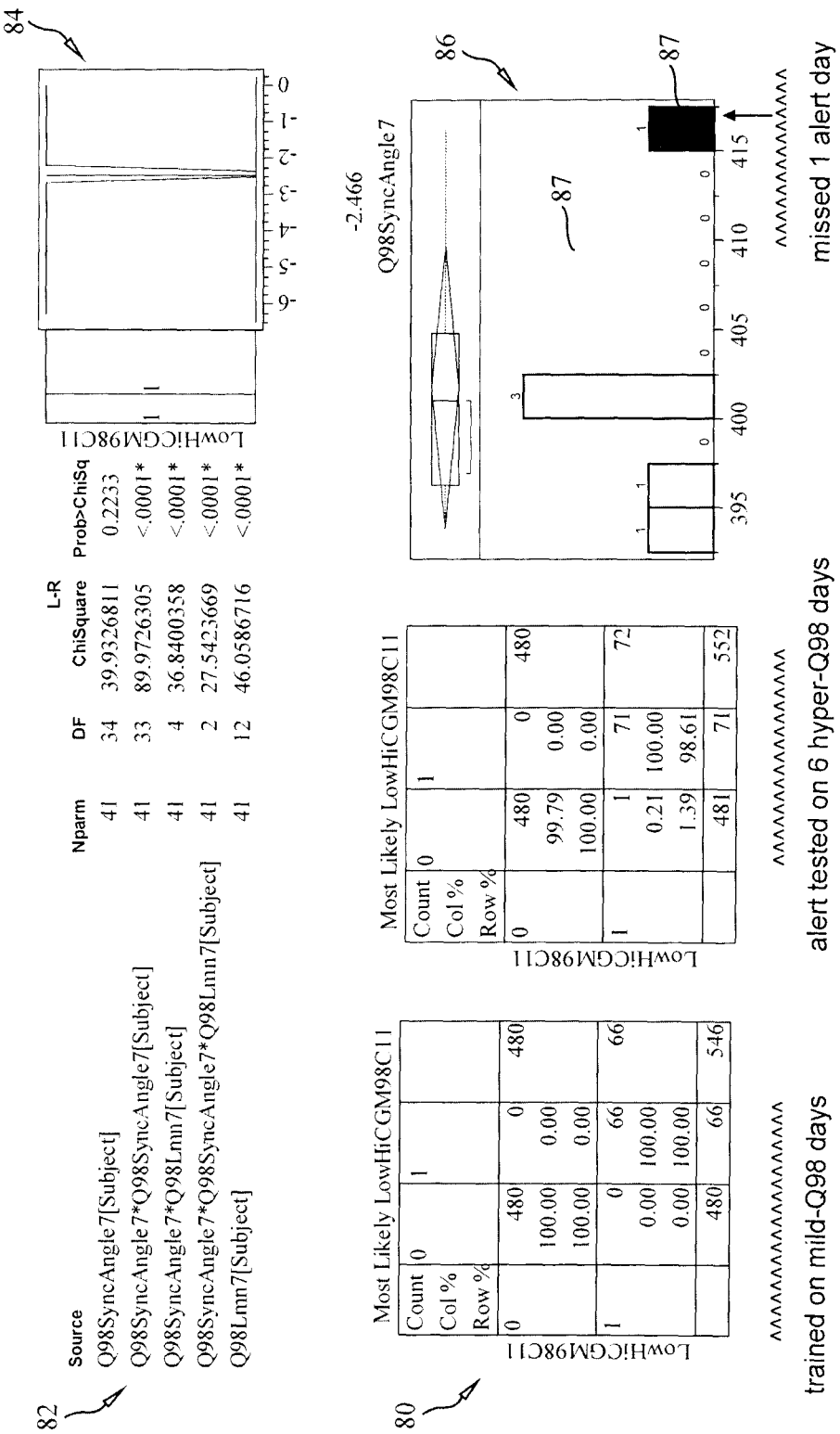
FIG. 21 illustrates a low risk Q98 model according to an embodiment of the present invention.

FIGS. 20 and 21 show the same results for Q98 alerts using predictor data near −3 radians (84) within 546 days of Q98 data. Chart (82) indicates 4 significant model Lorenz terms. Truth table (80) indicates >98% correct predictions on predictions and alert extrapolations. The alert bar chart shows one missed alert 87 (dark shaded).

Figure 22:
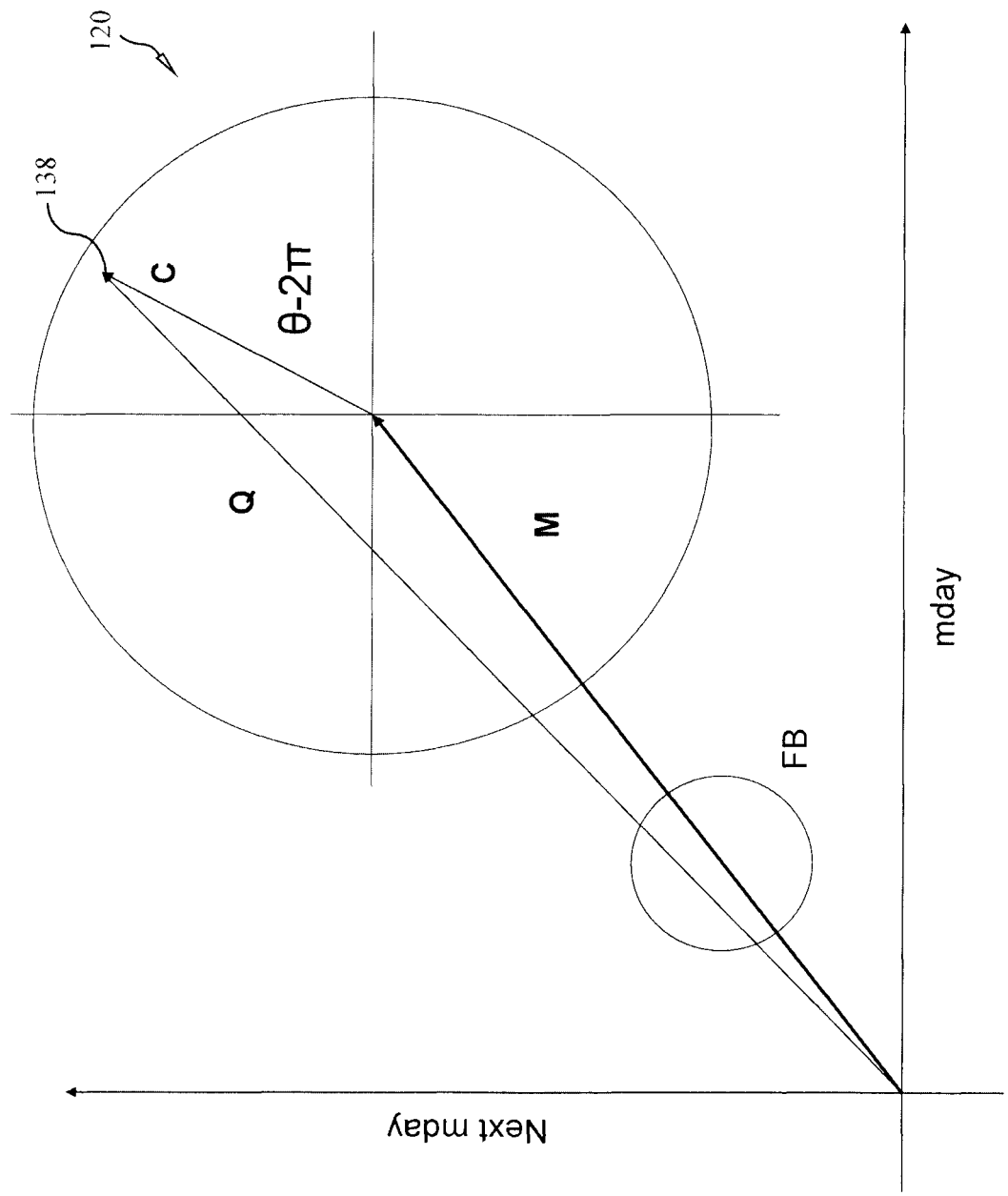
FIG. 22 is a Lorenz two-metric vector diagram according to an embodiment of the present invention.

FIG. 22 is a vector diagram 120 relating two metrics and their synchronized property to the Q-centroid 138 ($C_Q$) instead of using the tracking definitions described above. A solution to this geometry is $$C_Q=(\sin(\theta)Q_{now}+\cos(\theta)Q_{next})/(\cos(\theta)+\sin(\theta)) \qquad (6)$$

Hence, without tracking Q but tracking a metric such as FB, one can estimate the Q centroid. The model needs this to predict next-day glycemia. In summary one has all information to predict glycemia: Q is the known distributional quantile, M is the metric centroid for Q, and FB is the popular fasting metric.. Theta estimated by FB and FB tracking is the proper counterclockwise geometric angle relative to the horizontal axis. Subtracting 2pi converts it to the clockwise rotations used in the Lorenz diagrams. The vector relation doesn't care about angle versions. The small circle captures FB orbits that provide the angle. The large circle captures Q orbits; however, the Q centroid M is calculated by $C_Q$ (as in equation (6) above.

Figure 23:
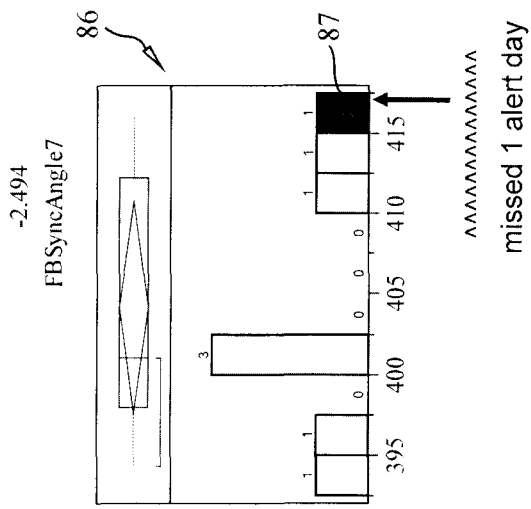
FIG. 23 illustrates a low risk FBQ98 model using combined metrics, according to an embodiment of the present invention.
Figure 24:
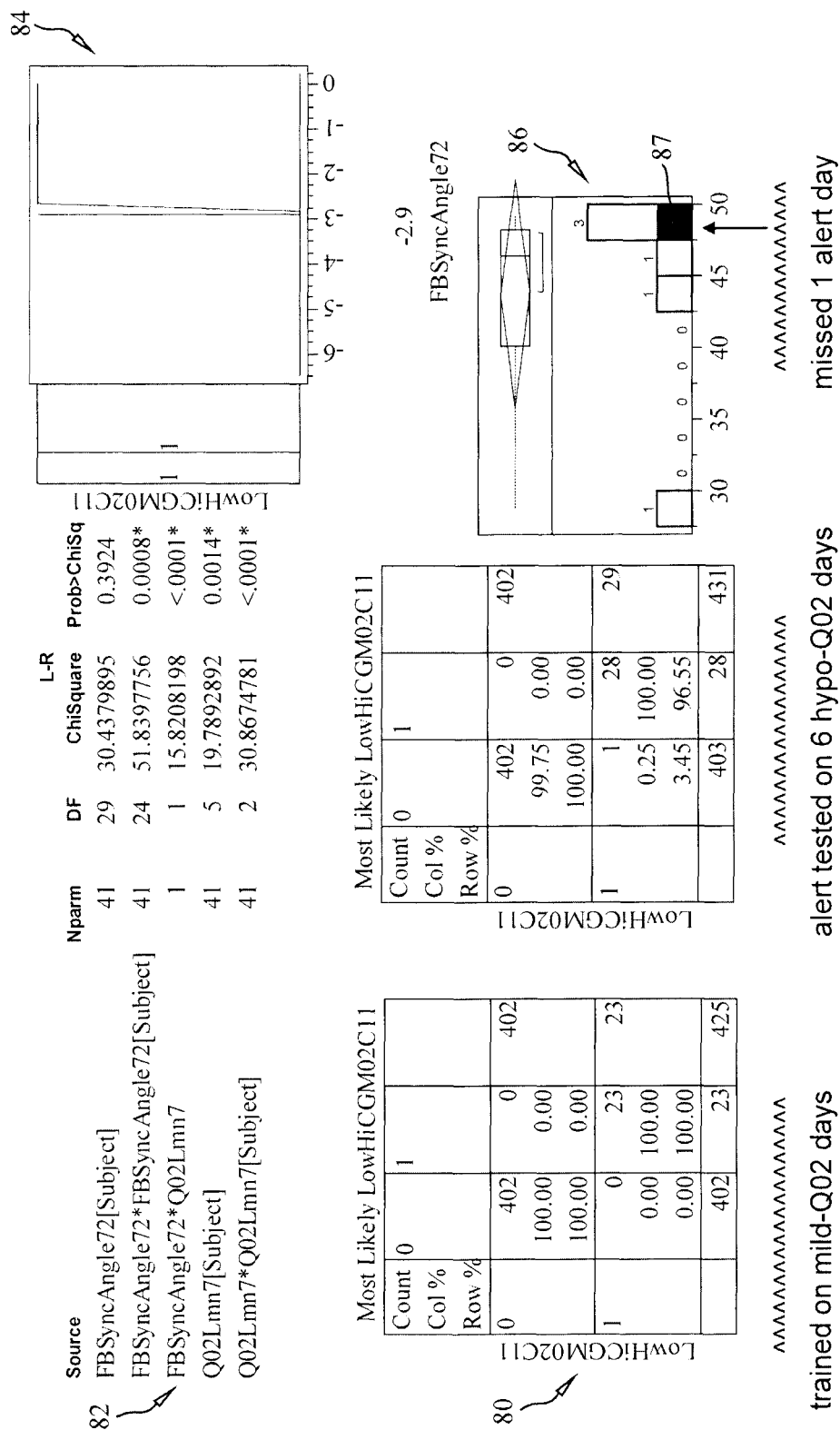
FIG. 24 illustrates a low risk FBQ02 model using combined metrics, according to an embodiment of the present invention.

FIGS. 23 and 24 show results from using such combined metric factors and sub-acute (non-acute defined above) extreme Q levels to develop a model system for prediction of impending episodes acute glycemia. This relates to the strategy depicted by FIGS. 17 to 21. FIG. 23 is like FIG. 21 and FIG. 24 is like FIG. 18 except FB data indicates Lorenz angle near −3 for evaluating Q98 properties using a CGM device; thereby significantly reducing patient data burden. Hence, we focus only on Q data near the critical angle near −3 radians. By FIG. 9 guidance and the alert-based histograms, this limited-Qdata method also works extremely well.

In FIG. 23 both FB and Q98 information are used in a model with 7 significant combination Lorenz terms (82). Tables (80) indicate >98% correct predictions and alerts with one missed alert call (shaded bar 87 in alert bar chart) 86.

In FIG. 24 both FB and Q02 information are used in a model with 4 significant combination Lorenz terms (82). Tables (80) indicate >96% correct predictions and alerts with one missed alert call (shaded section 87 in alert bar chart 86).

Figure 25:
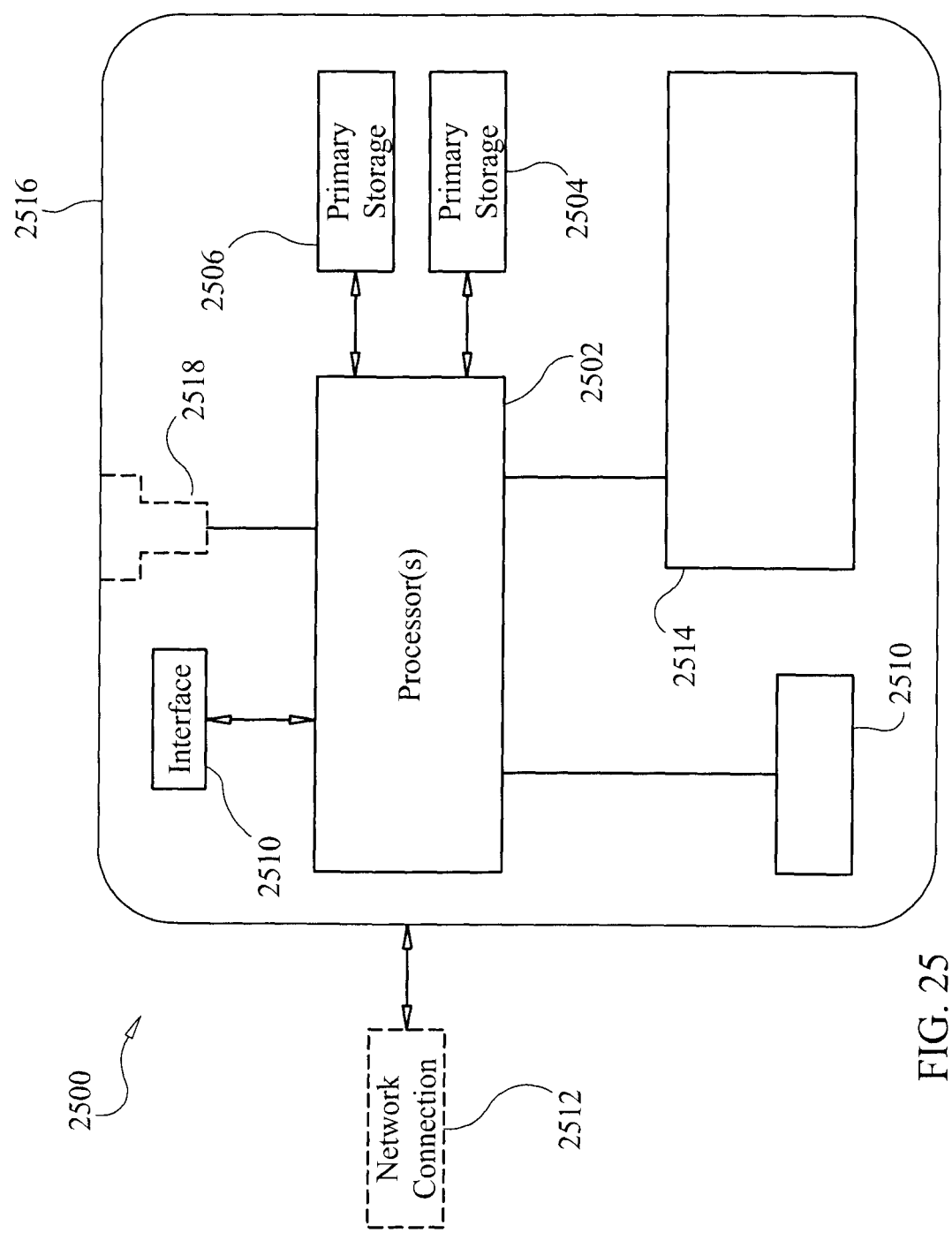
FIG. 25 is a schematic illustration of a blood glucose monitoring device according to an embodiment of the present invention.

FIG. 25 is a schematic illustration of a blood glucose monitoring device 2500 according to an embodiment of the present invention. Device 2500 includes a main body 2516 that houses one or more processors 502 (also referred to as central processing units, or CPUs) that are coupled to memory, including at least one of primary storage 2506 (typically a random access memory, or RAM) and primary storage 2504 (typically a read only memory, or ROM). As is well known in the art, primary storage 2504 acts to transfer data and instructions uni-directionally to the CPU and primary storage 2506 is used typically to transfer data and instructions in a bi-directional manner Both of these primary storage devices may include any suitable computer-readable media such as those containing instructions for carry out the algorithms and procedures described above for predicting acute glycemia. Storage 2504 and/or 2506 may be used to store programs for processing blood glucose data and storage 2506 may be used to store data such as blood glucose values from blood glucose readings/samplings, and results from processing the blood glucose values from the blood glucose readings.

An interface 2510, at least part of which may be operated by a user to carry out various operations, such as changing modes of values displayed on the display 2514 is provided. Also interfacing with the processor 2502 is a port that receive a blood glucose monitoring strip that is used to take a blood sample, and from which the processor 250 calculates a blood glucose reading in a manner known in the art. Optionally, the device 2500 may be connectable to a network, such as the Internet, and/or to a private network, such as by WiFi, Bluetooth, or the similar types of connectivity. This connectivity can be used to export blood glucose readings data and/or data used to predict acute glycemia achieved by processing according to techniques described above.

In addition, embodiments of the present invention further relate to computer readable media or computer program products that include program instructions and/or data (including data structures) for performing various computer-implemented operations. The media and program instructions may be those specially designed and constructed for the purposes of the present invention, or they may be of the kind well known and available to those having skill in the computer software arts. Examples of computer-readable media include, but are not limited to, magnetic media such as hard disks, floppy disks, and magnetic tape; flash drive devices, optical media such as CD-ROM, CDRW, DVD-ROM, or DVD-RW disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Figure 26:
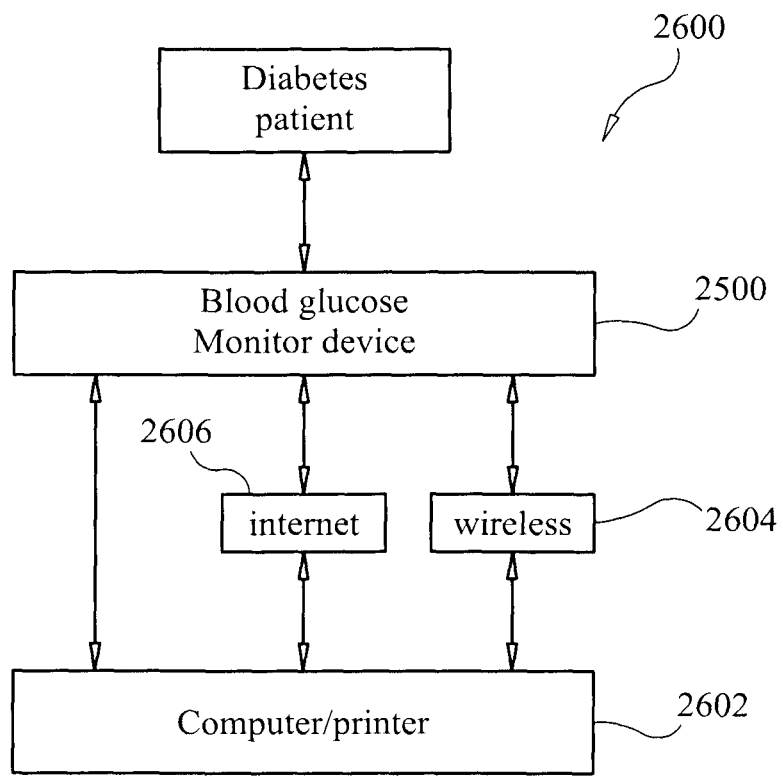
FIG. 26 is a block diagram illustrating components of a diagnostic system for use on a patient, according to an embodiment of the present invention.

FIG. 26 is a schematic illustration of a typical AG diagnostic system 2600 that may be used to perform procedures described above. The monitoring device 2500 provides serial BG values to be processed by the techniques described herein for predicting acute glycemia. The processing may be carried out in the processor(s) 2502 of the device, or, alternatively, the BG values can be outputted from the monitoring device 2500 to an external computer 2602 that can perform the processing. Further alternatively, if the device 2500 processes the BG values, the results from processing can be outputted to an external computer 2602 for storage and/or further output such as by printing, or can be outputted directly to a printer for printing. Outputting can be wireless, such as described above, or wired, either by direct connection 2604 to the computer or printer 2602, or over a network 2606, such as the Internet or other network. Time series and/or statistical analysis of the geometric flow patterns in the BG phase plots provide the critical information on the diabetic status and their trends for each patient and hence prediction of acute glycemia.

Figure 27:
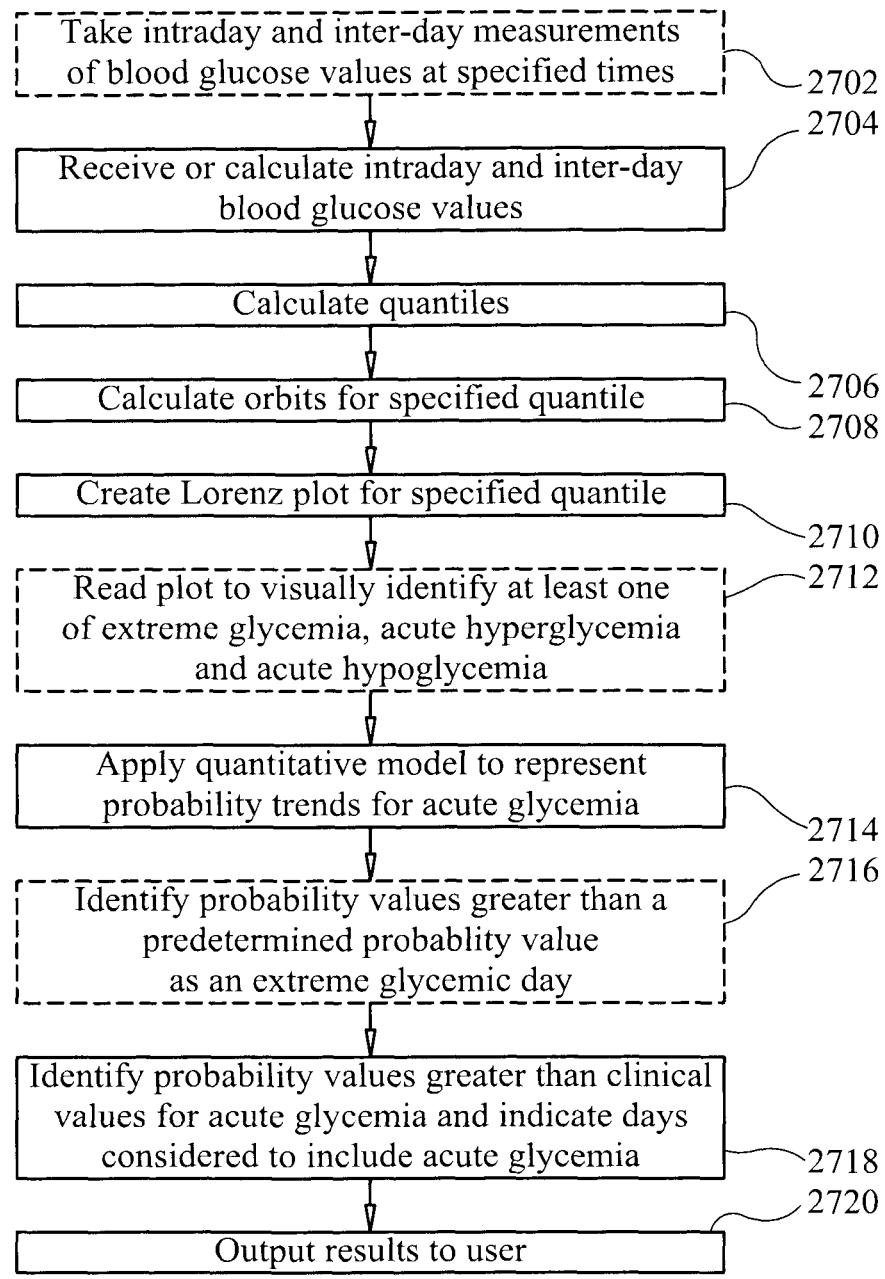
FIG. 27 shows events that may be carried out for predicting acute glycemia in a living body according to an embodiment of the present invention.

FIG. 27 shows events that may be carried out for predicting acute glycemia in a living body according to an embodiment of the present invention. Processing of events are carried out by one or more processors of an apparatus according to an embodiment of the present invention., one or more or all of which may be incorporated into a handheld personal blood glucose monitoring device 2500, such as by modifying a commercially available blood glucose monitoring device such as the ONE TOUCH® ULTRA® 2 Blood Glucose Monitor (Lifescan, Inc., Milpitas, California) or any other commercially available blood glucose monitor. Additionally or alternatively, some or all events can be carried out by one or more processors located externally of a blood glucose monitoring device (e.g., external computer 2602), using blood glucose readings taken from the blood glucose monitoring device 2500 or from multiple glucose monitoring devices or clinical blood monitoring instrumentation. Still further alternatively, these events can be performed by non-portable apparatus including blood monitoring capability, such as apparatus in a hospital, lab or doctor's office. Optionally, at event 2702, intra-day and inter-day blood glucose measurements can be made at specified times. Alternatively, the system may receive blood glucose values from an external source. At event 2704, intra-day and inter-day blood glucose values are either received or calculated from the blood glucose values. Optionally, the blood glucose values may be normalized.

At event 2706 at least one quantile of the blood glucose values are calculated. At event 2708 orbits are calculated for at least one specified quantile. Typically orbits are calculated for at least two quantiles preselected as being representative of potential acute hypoglycemia and potential acute hyperglycemia, respectively, such as Q02% and Q98% quantiles, or other preselected quantiles.

At event 2710 a Lorenz plot is created for at least one specified quantile, each of which may be a predetermined quantile. The Lorenz plot(s) can be displayed on the display of a device, such as on display 2514 or on the display of another system, such as an external computing device monitor. Further optionally, the Lorenz plot(s) can be outputted to a printer where they can be printed out and/or exported for review by other parties, or storage and/or can be stored internally in the device that created the plot(s). On a daily basis, this invention is a real-time device.

At optional event 271, the Lorenz plot(s) can be read/reviewed by a user to visually identify days exhibiting any of extreme glycemia, acute hypoglycemia and/or acute hyperglycemia.

At event 2714, the system can apply one or more of the quantitative models described herein to determine probability trends for acute glycemia. At optional event 2716, the system identifies probability values greater than a predetermined probability value as values associated with days exhibiting extreme glycemia. At event 2718, the system identifies probability values greater than clinical values for acute glycemia and identifies those days considered to include extreme glycemia for the quantile considered.

At event 2720, the system outputs results which may include identification of days of extreme glycemia, day of acute glycemia, and or predictions as to when one or more days including extreme glycemia and/or acute glycemia are expected in the future.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A device for tracking and forecasting glycemic levels in a patient, said device comprising:
    a housing;
    a processor coupled to a memory;
    a display configured to display a user interface and operatively connected to said processor, wherein the user interface is configured to receive at least one input from a user; and
    a port configured to receive a blood glucose monitoring strip, or needle prick, or skin fluids pump, wherein said device is configured to receive a blood glucose related sample from a patient and
    a transducer operatively connected to said port and configured to generate blood glucose values from blood glucose samples of the patient taken over a period of time;
    wherein said processor, said display, said port and said transducer are contained in said housing, and
    wherein said processor is configured with machine-executable instructions to: receive a time-ordered sequence of blood glucose values taken over a defined period of time from the transducer,
    calculate at least one quantile of said time-ordered sequence of blood glucose values taken over the period of time, calculate an orbit centroid by weighted averaging said time-ordered sequence of blood glucose quantile values taken over an increasing sequence of time-ordered periods of time of at least one quantile,
    create a Lorenz phase plot of the at least one quantile time-ordered sequence of blood glucose values by plotting a blood glucose quantile value in the at least one quantile sequence as a function of an immediate previous blood glucose quantile value in said at least one quantile sequence, wherein the Lorenz phase plot defines an orbit which flows about the orbit centroid and wherein the orbit is defined as a series of adjacent vectors each connecting a blood glucose quantile value with a previous blood glucose quantile value and each adjacent vector comprising a vector coordinate, identify a probability trend for acute glycemia by applying a quantitative model to the orbit defined in the Lorenz phase plot, identify a risk of impeding acute glycemia by determining vector position and a change in an angle between said adjacent vectors and a direction of said change, and
    wherein the device is configured to display the created Lorenz phase plot, the identified probability trend for acute glycemia and a notification of the risk of impending acute glycemia event based on the identified vector position and change in the angle and the direction of said change, wherein a change in the angle of −60 degrees indicates a risk of acute glycemia within 24 hours, as further indicated by a previous orbital section with recurrent position proximal to the said orbital position.

2. The device of claim 1, wherein the calculated at least one quantile comprises a Q98 quantile or a Q02 quantile or a combination thereof.

3. The device of claim 2, wherein the impending acute glycemia comprises an impending hypoglycemia event or an impending hyperglycemia event.

4. The device of claim 3, wherein said processor is configured to identify and forecast, days in which extreme glycemia was experienced by the patient and wherein said display is configured to display the days in which said extreme glycemia was experienced by the patient.

5. The device of claim 4, wherein the period of time includes a 24-hour day and wherein the processor is configured to identify and forecast days within the sequence of multiple days in which the patient will experience acute glycemia.

* * * * *